United States Patent
Kajikawa et al.

(10) Patent No.: US 9,499,830 B2
(45) Date of Patent: Nov. 22, 2016

(54) GENE INDUCING ELONGATION OF ROOTS OR INCREASING BIOMASS, AND USE THEREFOR

(75) Inventors: Masataka Kajikawa, Ikoma (JP); Akiho Yokota, Ikoma (JP); Kinya Akashi, Ikoma (JP); Seja Gasenone Maphanyane, Gaborone (BW); Pharoah Mosupi, Gaborone (BW); Stephen Majara Chite, Gaborone (BW); Norio Kato, Iwata (JP)

(73) Assignees: NATIONAL UNIVERSITY CORPORATION NARA INSTITUTE OF SCIENCE AND TECHNOLOGY, Ikoma-shi, Nara (JP); THE REPUBLIC OF BOTSWANA, Gaborone (BW)

( * ) Notice: Subject to any disclaimer, the term of this patent is extended or adjusted under 35 U.S.C. 154(b) by 106 days.

(21) Appl. No.: 14/234,524

(22) PCT Filed: Jul. 24, 2012

(86) PCT No.: PCT/JP2012/068729
§ 371 (c)(1),
(2), (4) Date: Jan. 23, 2014

(87) PCT Pub. No.: WO2013/015287
PCT Pub. Date: Jan. 31, 2013

(65) Prior Publication Data
US 2014/0165232 A1 Jun. 12, 2014

(30) Foreign Application Priority Data
Jul. 25, 2011 (JP) .................... 2011-162036

(51) Int. Cl.
*C12N 15/29* (2006.01)
*C12N 15/82* (2006.01)
*C07K 14/415* (2006.01)

(52) U.S. Cl.
CPC ......... *C12N 15/8261* (2013.01); *C07K 14/415* (2013.01)

(58) Field of Classification Search
None
See application file for complete search history.

(56) References Cited

U.S. PATENT DOCUMENTS
2009/0055971 A1  2/2009  Akashi et al.
2009/0144847 A1  6/2009  Shaikh et al.

FOREIGN PATENT DOCUMENTS
JP        2004-187564 A     7/2004
WO    WO 2009/094401 A2   7/2009

OTHER PUBLICATIONS

Cheng et al. The Plant Journal (2005) 43, 758-768).*
Robson et al. (The Plant Journal (2001) 28(6), 619-631).*
Guo et al (2004, Proc. Natl. Acad. Sci. USA 101: 9205-9210).*
Gilleland et al. BioTechniques 25:948-954 (Dec. 1998).*
English translation of International Preliminary Report on Patentability and Written Opinion mailed Feb. 6, 2014, in PCT International Application No. PCT/JP2012/068729.
Datta et al., "Arabidopsis CONSTANS-LIKE3 is a Positive Regulator of Red Light Signaling and Root Growth", The Plant Cell, vol. 18, Jan. 2006, pp. 70-84.
Doerner et al., "Control of root growth and development by cyclin expression", Nature, vol. 380, Apr. 11, 1996, pp. 520-523.
International Search Report for PCT/JP2012/068729 mailed on Aug. 28, 2012.
Morris et al., "Day Neutral Flowering Represses CONSTANS to Prevent Arabidopsis Flowering Early in Short Days", The Plant Cell, vol. 22, Apr. 2010, pp. 1118-1128.
Nishimura et al., "Yaseishu Suika ni Okeru Kanso Yudo Idenshi no Tanri Oyobi Sono Hatsugen Kaiseki (Isolation of Drought-Inducible Gene from Wild Watermelon and Analysis of Expression of the Gene)", Journal of the Agricultural Chemical Society of Japan, #B12, 2001, vol. 75, No. 4, p. 529.
Ryu et al., "The Arabidopsis C3H2C3-Type RING E3 Ubiquitin Ligase AtAIRP1 Is a Positive Regulator of an Abscisic Acid-Dependent Response to Drought Stress", Plant Physiology, vol. 154, Dec. 2010, pp. 1983-1997.
Yoshida et al., "Kanso Kyo-Hikari Taisei no Yaseishu Suika o Mochiita Proteome Kaiseki: Ha ni Okeru Stress Otosei Tanpakushitsu (Proteome Analysis Using Wild Watermeron Having Drought and Strong Light Resistance: Stress-Responsive Proteins in Leaves)", Japan Society for Bioscience, Biotechnology, and Agrochemistry Taikai Koen Yoshishu, #29H027α, 2005, p. 144.
Yoshimura et al., "Kyo-Hikari Kanso Stress ni Taisuru Yaseishu Suika no Ne no Outou (Response of Roots of Wild Watermelon to Strong Light and Drought Stress)", Japan Society for Bioscience, Biotechnology, and Agrochemistry Taikai Koen Yoshishu, #29H026β, 2005, p. 144.
Zhang et al., "Maize ABP9 enhances tolerance to multiple stresses in transgenic Arabidopsis by modulating ABA signaling and cellular levels of reactive oxygen species", Plant Molecular Biology, vol. 75, Feb. 17, 2011, pp. 365-378.
Extended European Search Report issued Jan. 8, 2015, in European Patent Application No. 12818107.0.

* cited by examiner

Primary Examiner — Anne Kubelik
Assistant Examiner — Charles Logsdon
(74) Attorney, Agent, or Firm — Birch, Stewart, Kolasch & Birch, LLP

(57) ABSTRACT

By increasing, in a plant, expression of a gene or the like encoding a novel CONSTANS-LIKE protein, it is possible to promote root elongation of the plant and/or increase biomass of the plant.

7 Claims, 8 Drawing Sheets

GENE INDUCING ELONGATION OF ROOTS OR INCREASING BIOMASS, AND USE THEREFOR

TECHNICAL FIELD

The present invention relates to (i) a novel gene inducing elongation of roots (root elongation) or increasing biomass and (ii) use of the novel gene.

BACKGROUND ART

Plants adapted to arid zones such as a desert are known to have excellent ability to elongate their roots, so as to reach a water vein deep under the ground in order to avoid drought stress. By introducing a gene related to this ability into a general crop, it is expected that a root of the plant is promoted to efficiently absorb soil moisture and/or nutrient sources, and whereby the plant achieves improved drought stress resistance and an increased yield. Further, since the root also involves supporting the plant body, development of the root is an important factor for improvement of productivity of the plant.

For this reason, researches on a gene regulating elongation of a plant's root have been conventionally conducted. For example, Patent Literature 1 describes a technique for (i) obtaining, by the T-DNA tagging technique, a mutant in which root elongation is outstandingly suppressed as compared with a wild strain and (ii) using a gene or the like relating to such a phenotype. Further, Non-Patent Literature 1 describes one example of overexpression of Cyclin gene, as an example of root elongation promotion by a gene introduction technique. Non-Patent Literature 2 reports that an *Arabidopsis thaliana* AtCOL3 gene knockout plant has a phenotype in which a lateral root elongation is suppressed.

CITATION LIST

Patent Literature

[Patent Literature 1]
Japanese Patent Application Publication, Tokukai, No. 2004-187564 A (Publication date: Jul. 8, 2004)

Non-Patent Literatures

[Non-Patent Literature 1]
Doerner et al., 1996 Nature, 380: 520-523
[Non-Patent Literature 2]
Datta et al., 2006 Plant Cell, 18: 70-84

SUMMARY OF INVENTION

Technical Problem

However, searches for the gene relating to the root development have not been conducted enough yet. Thus, there are strong demands for (i) finding a gene inducing root elongation and (ii) developing a technique for using the gene, e.g., a technique for developing a drought tolerant plant.

The present invention was made in view of the foregoing problem, and has an object to identify a novel gene inducing root elongation and to provide the gene together with a technique for using the gene.

Solution to Problem

The inventors of the present invention made diligent studies in order to attain the above object, and analyzed genetic information and molecular mechanism of plants living in the arid zones such as a desert, so as to find a gene that induces root elongation when expression of the gene is increased. The inventors further proceeded with the study, so as to find that transforming the gene into a plant leads to not only the root elongation but also an increase in biomass. Thus, the inventors completed the present invention. Namely, the present invention has the following aspects:

(1) A method for producing a plant in which root elongation is induced or whose biomass is increased, including the step of:

increasing, in a plant, expression of a gene selected from the group consisting of the following (a) through (e):

(a) a gene encoding a protein having the amino acid sequence of SEQ ID NO: 1;

(b) a gene encoding a protein having an amino acid sequence with substitution, deletion, insertion, and/or addition of one or several amino acid residues in the amino acid sequence of SEQ ID NO: 1, the protein having (i) an activity of inducing root elongation of a plant or (ii) an activity of increasing biomass of a plant;

(c) a gene encoding a protein having an amino acid sequence having at least 80% homology to the amino acid sequence of SEQ ID NO: 1, the protein having (i) an activity of inducing root elongation of a plant or (ii) an activity of increasing biomass of a plant;

(d) a gene having the nucleotide sequence of SEQ ID NO: 2; and (e) a gene that hybridizes under stringent conditions with a polynucleotide having a nucleotide sequence which is complementary to a nucleotide sequence of any one of the polynucleotides (a) through (d), the gene encoding a protein having (i) an activity of inducing root elongation of a plant or (ii) an activity of increasing biomass of a plant.

(2) The method described in (1), wherein:

the step of increasing expression of the gene includes a step of producing a transformed plant cell by introducing, into a plant cell, a gene selected from the group consisting of (a) through (e) recited in claim 1.

(3) The method described in (2), further including the step of:

reproducing a plant body from the transformed plant cell.

(4) A plant in which root elongation is induced or whose biomass is increased, said plant being transformed by a gene selected from the group consisting of the following (a) through (e):

(a) a gene encoding a protein having the amino acid sequence of SEQ ID NO: 1;

(b) a gene encoding a protein having an amino acid sequence with substitution, deletion, insertion, and/or addition of one or several amino acid residues in the amino acid sequence of SEQ ID NO: 1, the protein having (i) an activity of inducing root elongation of a plant or (ii) an activity of increasing biomass of a plant;

(c) a gene encoding a protein having an amino acid sequence having at least 80% homology to the amino acid sequence of SEQ ID NO: 1, the protein having (i) an activity of inducing root elongation of a plant or (ii) an activity of increasing biomass of a plant;

(d) a gene having the nucleotide sequence of SEQ ID NO: 2; and (e) a gene that hybridizes under stringent conditions with a polynucleotide having a nucleotide sequence which is complementary to a nucleotide sequence of any one of the polynucleotides (a) through (d), the gene encoding a protein having (i) an activity of inducing root elongation of a plant or (ii) an activity of increasing biomass of a plant.

(5) A plant in which root elongation is induced and/or whose biomass is increased, said plant including a gene selected from the group consisting of the following (a) through (e), expression of the gene being increased in said plant:
  (a) a gene encoding a protein having the amino acid sequence of SEQ ID NO: 1;
  (b) a gene encoding a protein having an amino acid sequence with substitution, deletion, insertion, and/or addition of one or several amino acid residues in the amino acid sequence of SEQ ID NO: 1, the protein having (i) an activity of inducing root elongation of a plant or (ii) an activity of increasing biomass of a plant;
  (c) a gene encoding a protein having an amino acid sequence having at least 80% homology to the amino acid sequence of SEQ ID NO: 1, the protein having (i) an activity of inducing root elongation of a plant or (ii) an activity of increasing biomass of a plant;
  (d) a gene having the nucleotide sequence of SEQ ID NO: 2; and
  (e) a gene that hybridizes under stringent conditions with a polynucleotide having a nucleotide sequence which is complementary to a nucleotide sequence of any one of the polynucleotides (a) through (d), the gene encoding a protein having (i) an activity of inducing root elongation of a plant or (ii) an activity of increasing biomass of a plant.

(6) A plant which is a progeny, an offspring, or a clone of a plant described in (4) or (5).

(7) A breeding material of a plant described in any one of (4) through (6).

(8) A method for inducing root elongation of a plant, including the step of:
  increasing expression of a gene selected from the group consisting of the following (a) through (e):
  (a) a gene encoding a protein having the amino acid sequence of SEQ ID NO: 1;
  (b) a gene encoding a protein having an amino acid sequence with substitution, deletion, insertion, and/or addition of one or several amino acid residues in the amino acid sequence of SEQ ID NO: 1, the protein having an activity of inducing root elongation of a plant;
  (c) a gene encoding a protein having an amino acid sequence having at least 80% homology to the amino acid sequence of SEQ ID NO: 1, the protein having an activity of inducing root elongation of a plant;
  (d) a gene having the nucleotide sequence of SEQ ID NO: 2; and
  (e) a gene that hybridizes under stringent conditions with a polynucleotide having a nucleotide sequence which is complementary to a nucleotide sequence of any one of the polynucleotides (a) through (d), the gene encoding a protein having an activity of inducing root elongation of a plant.

(9) A method for increasing biomass of a plant, including the step of:
  increasing expression of a gene selected from the group consisting of the following (a) through (e):
  (a) a gene encoding a protein having the amino acid sequence of SEQ ID NO: 1;
  (b) a gene encoding a protein having an amino acid sequence with substitution, deletion, insertion, and/or addition of one or several amino acid residues in the amino acid sequence of SEQ ID NO: 1, the protein having an activity of increasing biomass of a plant;
  (c) a gene encoding a protein having an amino acid sequence having at least 80% homology to the amino acid sequence of SEQ ID NO: 1, the protein having an activity of increasing biomass of a plant;
  (d) a gene having the nucleotide sequence of SEQ ID NO: 2; and
  (e) a gene that hybridizes under stringent conditions with a polynucleotide having a nucleotide sequence which is complementary to a nucleotide sequence of any one of the polynucleotides (a) through (d), the gene encoding a protein having an activity of increasing biomass of a plant.

(10) A method for producing a plant body, including the steps of:
  preparing transformed plants in each of which expression of a gene selected from the group consisting of the following (a) through (e) is increased; and
  measuring (i) root elongation and/or (ii) biomass of each of progeny plants of the transformed plants and, among the progeny plants, selecting a line in which (i) the root elongation and/or (ii) the biomass is significantly improved,
  (a) a gene encoding a protein having the amino acid sequence of SEQ ID NO: 1;
  (b) a gene encoding a protein having an amino acid sequence with substitution, deletion, insertion, and/or addition of one or several amino acid residues in the amino acid sequence of SEQ ID NO: 1, the protein having (i) an activity of inducing root elongation of a plant or (ii) an activity of increasing biomass of a plant;
  (c) a gene encoding a protein having an amino acid sequence having at least 80% homology to the amino acid sequence of SEQ ID NO: 1, the protein having (i) an activity of inducing root elongation of a plant or (ii) an activity of increasing biomass of a plant;
  (d) a gene having the nucleotide sequence of SEQ ID NO: 2; and
  (e) a gene that hybridizes under stringent conditions with a polynucleotide having a nucleotide sequence which is complementary to a nucleotide sequence of any one of the polynucleotides (a) through (d), the gene encoding a protein having (i) an activity of inducing root elongation of a plant or (ii) an activity of increasing biomass of a plant.

(11) A gene selected from the group consisting of the following (a) through (e):
  (a) a gene encoding a protein having the amino acid sequence of SEQ ID NO: 1;
  (b) a gene encoding a protein having an amino acid sequence with substitution, deletion, insertion, and/or addition of one or several amino acid residues in the amino acid sequence of SEQ ID NO: 1, the protein having (i) an activity of inducing root elongation of a plant or (ii) an activity of increasing biomass of a plant;
  (c) a gene encoding a protein having an amino acid sequence having at least 80% homology to the amino acid sequence of SEQ ID NO: 1, the protein having (i) an activity of inducing root elongation of a plant or (ii) an activity of increasing biomass of a plant;
  (d) a gene having the nucleotide sequence of SEQ ID NO: 2; and
  (e) a gene that hybridizes under stringent conditions with a polynucleotide having a nucleotide sequence which is complementary to a nucleotide sequence of any one of the polynucleotides (a) through (d), the gene encoding a protein having (i) an activity of inducing root elongation of a plant or (ii) an activity of increasing biomass of a plant.

(12) A protein selected from the group consisting of the following (f) through (i):
  (f) a protein having the amino acid sequence of SEQ ID NO: 1;
  (g) a protein having an amino acid sequence with substitution, deletion, insertion, and/or addition of one or several amino acid residues in the amino acid sequence of SEQ ID NO: 1, the protein having (i) an activity of inducing root elongation of a plant or (ii) an activity of increasing biomass of a plant;

(h) a protein having an amino acid sequence having at least 80% homology to the amino acid sequence of SEQ ID NO: 1, the protein having (i) an activity of inducing root elongation of a plant or (ii) an activity of increasing biomass of a plant; and (i) a protein encoded by a gene described (11).

(13) A recombinant expression vector including a gene described in (11).

(14) A transformant into which a gene described in (11) or a recombinant expression vector described in (13) is introduced.

(15) The transformant described in (14), wherein said transformant is a plant.

(16) An agent including, as an active element, a gene described in (11) or a recombinant expression vector described in (13), said agent inducing root elongation of a plant or increasing biomass of a plant.

(17) A polynucleotide selected from the group consisting of the following (j) through (l):

(j) a polynucleotide having the nucleotide sequence of SEQ ID NO: 3;

(k) a polynucleotide having a nucleotide sequence with deletion, substitution, or addition of one or several nucleotides in the nucleotide sequence of SEQ ID NO: 3, the polynucleotide having a function as a promoter of regulating expression of a target gene in response to drought stress on a plant; and (l) a polynucleotide that hybridizes under stringent conditions with a polynucleotide having a nucleotide sequence which is complementary to a nucleotide sequence of the polynucleotide (j) or (k), the polynucleotide having a function as a promoter of regulating expression of a target gene in response to drought stress on a plant.

(18) A recombinant expression vector including, as a promoter, a polynucleotide described in (1'7).

(19) A transformant into which a polynucleotide described in (17) or a recombinant expression vector described in (18) is introduced.

Advantageous Effects of Invention

The gene of the present invention is a novel gene having the activity of inducing root elongation of a plant or the activity of increasing biomass of a plant. According to the gene of the present invention and the technique of using the gene, it is possible to obtain a plant in which root elongation is induced or a plant whose biomass is increased. Such the plant has advantages of, for example, not only improved drought resistance and stability but also increased biomass.

BRIEF DESCRIPTION OF DRAWINGS (a) of FIG. 1 shows how a water content in the soil changes. (b) of FIG. 1 shows roots of wild watermelons grown for 0 through 4 days under dry conditions or wet conditions.

DESCRIPTION OF EMBODIMENTS

Figure 1:
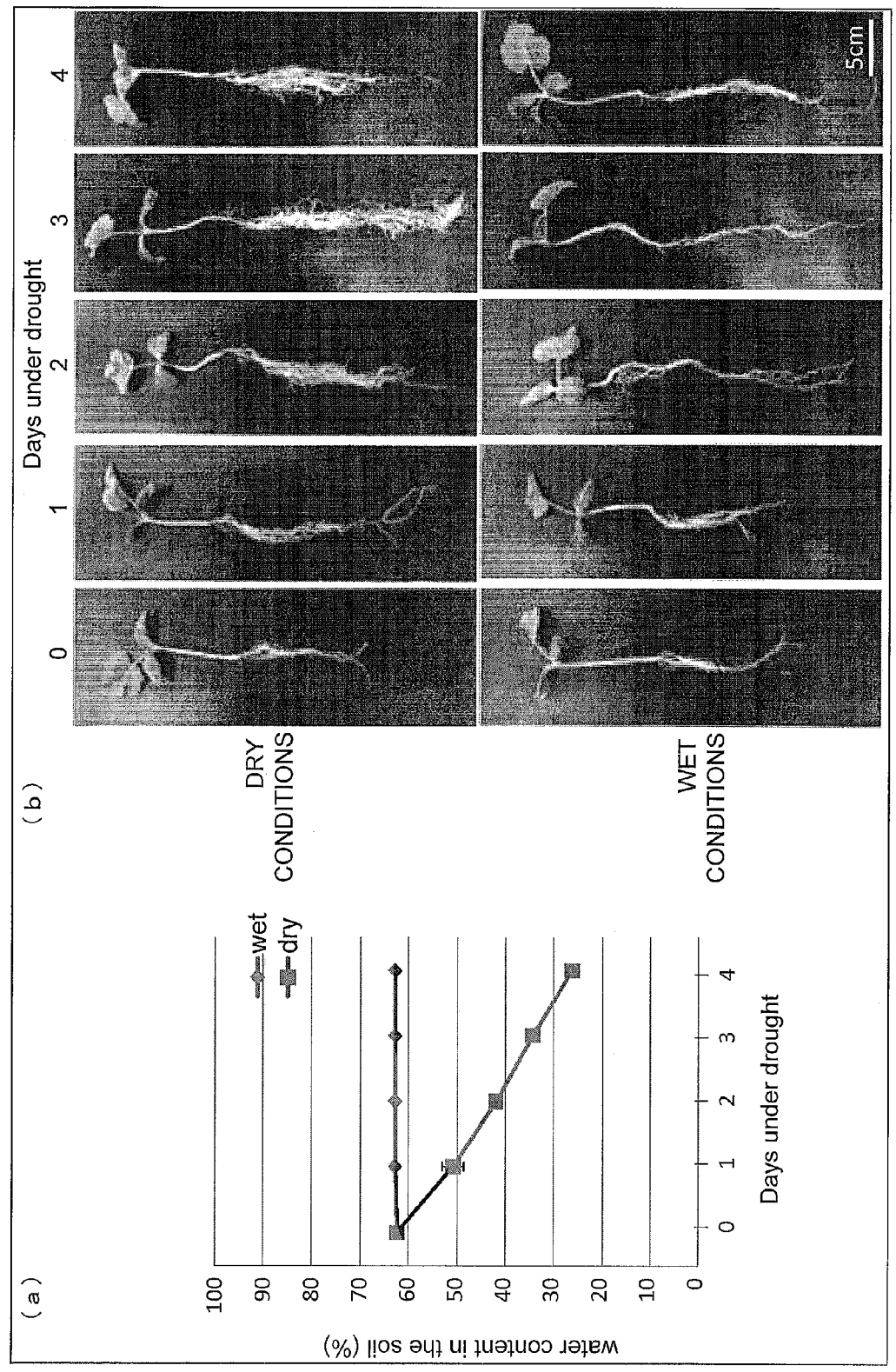

The following describes embodiments of the present invention in detail. Note that all professional literatures and all patent literatures described herein are quoted as references to the present invention. Unless otherwise specially mentioned, the expression "A through B" or "from A to B" expressing a numerical range means "A or more (i.e., including A and more than A) and B or less (i.e., including B and less than B).

Bases (nucleotides) and amino acids herein are indicated as appropriate by a one letter code or a three letter code as specified by the IUPAC and the IUB. As used herein, the term "protein" is used interchangeably with a "peptide" or a "polypeptide". Further, the term "gene" is used interchangeably with a "polynucleotide", "nucleic acid", or a "nucleic acid molecule", and intends a polymer of nucleotides. Here, the gene can exist in the form of DNA (for example, cDNA or a genomic DNA) or in the form of RNA (for example, mRNA). The DNA or the RNA may be double-stranded or single-stranded. The single-stranded DNA or RNA may be a coding strand (sense strand) or a noncoding strand (antisense strand). The gene may be synthesized chemically, and may be modified so that codon usage is changed in order to improve expression of a protein encoded by the gene. Of course, the gene may be modified so that a codon is substituted with another codon, provided that these codons encode the same amino acid. Further, in a case where the gene is the one encoding a protein, that gene includes DNA having a desired nucleotide sequence based on degeneracy of genetic code.

<1. Gene and Protein>

A gene of the present invention is a gene selected from the group consisting of the following (a) through (e): (a) a gene encoding a protein having the amino acid sequence of SEQ ID NO: 1; (b) a gene encoding a protein having an amino acid sequence with substitution, deletion, insertion, and/or addition of one or several amino acid residues in the amino acid sequence of SEQ ID NO: 1, the protein having (i) an activity of inducing root elongation of a plant or (ii) an activity of increasing biomass of a plant; (c) a gene encoding a protein having an amino acid sequence having at least 80% homology to the amino acid sequence of SEQ ID NO: 1, the protein having (i) an activity of inducing root elongation of a plant or (ii) an activity of increasing biomass of a plant; (d) a gene having the nucleotide sequence of SEQ ID NO: 2; and (e) a gene that hybridizes under stringent conditions with a polynucleotide having a nucleotide sequence which is complementary to a nucleotide sequence of any one of the polynucleotides (a) through (d), the gene encoding a protein having (i) an activity of inducing root elongation of a plant or (ii) an activity of increasing biomass of a plant.

A protein of the present invention is a protein selected from the group consisting of the following (f) through (i): (f) a protein having the amino acid sequence of SEQ ID NO: 1; (g) a protein having an amino acid sequence with substitution, deletion, insertion, and/or addition of one or several amino acid residues in the amino acid sequence of SEQ ID NO: 1, the protein having (i) an activity of inducing root elongation of a plant or (ii) an activity of increasing biomass of a plant; (h) a protein having an amino acid sequence having at least 80% homology to the amino acid sequence of SEQ ID NO: 1, the protein having (i) an activity of inducing root elongation of a plant or (ii) an activity of increasing biomass of a plant; and (i) a protein encoded by a gene of any one of (a) through (e) above.

Each of the genes of (a) through (e) encodes a protein having (i) the activity of inducing root elongation of a plant or (ii) the activity of increasing biomass of a plant, i.e., any one of the proteins of (f) through (i). Thus, by, e.g., increasing expression of any one of the genes in a plant, it is possible to promote root elongation of a plant or to increase biomass of a plant.

First, specific explanations are given to the gene of (a) and the protein of (f). SEQ ID NO: 1 shows the amino acid sequence of CLCOL1 protein derived from a wild watermelon (*Citrullus lanatus* sp. No. 101117-1). CLCOL1 protein is a protein consisting of 337 amino acids, and is assumed to function as a CONSTANS-like transcription factor. So far, functions of CLCOL1 protein have not been known well. However, in the study leading to the present invention, the inventors of the present invention found that CLCOL1 protein has a function of inducing (promoting) root elongation or increasing biomass of a plant.

It is known that the wild watermelon lives in the arid zones such as a desert, and has (i) an ability of elongating its root even under severe dry conditions and (ii) high durability against drought stress. As stated in the later-described Examples, in the study leading to the present invention, the inventors of the present invention found that expression of CLCOL1 gene is induced in the root of the wild watermelon, particularly in the tip of the root (root tip), at an early timing of drought stress. Further, as a result of analysis of sequence information, the inventors identified that CLCOL1 gene encodes the CONSTANS-like transcription factor.

Expression of CLCOL1 gene was induced in a hairy root of the wild watermelon, with the result that elongation of the root was promoted as compared with a control plant in which no induction was carried out. Conversely, a line of a wild watermelon in which that function was inhibited in its hairy root was produced, with the result that root elongation was inhibited therein. Further, a line of *Arabidopsis thaliana* in which CLCOL1 gene was constantly overexpressed was produced, with the result that elongation of a main root thereof was promoted. These results show that CLCOL1 gene functions as a key factor of regulation on promotion of root elongation of the wild watermelon in response to the dry conditions. Further, the above gene was transformed into a plant, with the result that such the transformation was shown to be capable of increasing biomass of a plant.

By using the gene of the present invention, it is possible to allow a plant to efficiently absorb soil moisture and/or nutrient sources so as to give the plant improved durability against drought stress and/or to increase a yield of a crop. Further, by using the gene of the present invention in a cultured cell line of a root of a plant, it is possible to produce a useful substance at a high yield.

The gene of (b) intends a gene encoding a protein (i.e., a protein of (g)) which is a mutant, a derivative, a variant, an allele, a homologue, an ortholog, a partial peptide, or a fusion protein with another protein or another peptide each of which is functionally equal to a protein having the amino acid sequence of SEQ ID NO: 1, the protein having the activity of inducing root elongation. There is no specific limitation on a sequence of the gene of (b).

The "protein having an activity of inducing root elongation of a plant" as used herein intends a protein having a function of, in a case where the protein is expressed in a plant (including a cultured cell), elongating and/or developing a root of the plant, particularly, inducing (promoting) elongation and/or development of a main root of the plant. Note that a tissue in which the protein is expressed may be, but is not limited to, a root. Namely, in other words, the above expression intends a protein being encoded by a target gene and having such an activity that, in a case where the protein is expressed in a plant, induces elongation of a root (or a cell derived from the root) of the plant and accelerates a speed at which the root (or the cell derived from the root) of the plant elongates (proliferates). In a case where expression or a function of a target gene in a plant is inhibited, this activity can be evaluated as an activity of suppressing root elongation of the plant. The expression or the function of the target gene in the plant can be inhibited by, for example, conventional techniques such as a known gene-disrupted strain producing technique or a known antisense technique.

The term "root" intends an organ by which a plant body is fixed to a base (for example, the earth), by which the plant body is supported, and via which the plant body absorbs components. The root encompasses not only a fibrous root of a monocotyledon and a main root of a dicotyledon but also an adventitious root, an aerial root, a brace root, a buttress root, an adhesive root, a parasitic root, a tuberous root, a water absorptive root, a respiratory root, a traction root, and a contractile root.

The term "biomass" as used herein intends a quantity of the whole of, a part of, or a separate organ of an individual plant or a combination thereof. Examples of the whole of, the part of, or the separate organ of the individual plant encompass the whole part, an above-ground part, a root, a stem, a leaf, a fruit, a seed, an embryo, an ovule, an ovary, a shoot apex, an anther, a pollen, and an ear. Examples of the quantity encompass a size, a length, a width, a weight, an area, and a volume. Thus, examples of the biomass encompass a weight of an entire part, a weight of an above-ground part, a yield, a stem diameter, the number of stems, a culm length, a leaf area, the number of leaves, the number of ears, the number of grains per ear, an ear length, a maximum ear length, and a total ear weight. The expression "increasing (increased)" may be an increase of any one of the above biomass quantities or a combination of some of the above biomass quantities. An indicator of the "increasing (increased)" can be, for example, a measurement of biomass of a plant body in comparison with a control plant (e.g., a parent plant or a nontransformant).

Here, there is no limitation on the number of amino acids which may be deleted, substituted, or added, as long as the above-described function is not lost. However, the number of amino acids which may be deleted, substituted, or added is the number of amino acids which can be deleted, substituted, or added by a known mutagenesis (mutation introduction) technique such as the site-directed mutagenesis. Typically, the number of amino acids which may be deleted, substituted, or added is 30 or less, preferably 20 or less, further preferably 10 or less, most preferably 5 or less (for example, 5, 4, 3, 2, 1 amino acid(s)). Whether or not a mutated protein gives a plant a desired trait can be determined by expressing a gene encoding the protein in a plant and determining whether or not root elongation is promoted in the plant or whether or not biomass of the plant is increased. The mutation herein mainly means a mutation artificially introduced into a target by, e.g., the site-directed mutagenesis, but may alternatively be a mutation similar to a naturally-existing one.

An amino acid residue to be mutated is preferably mutated into another amino acid in which a characteristic of a side chain of the amino acid residue is preserved. Examples of the characteristic of the side chain of the amino acid encompass hydrophobic amino acids (A, I, L, M, F, P, W, Y, V), hydrophilic amino acids (R, D, N, C, E, Q, G, H, K, S, T), amino acids having an aliphatic side chain (G, A, V, L, I, P), amino acids having a hydroxyl group-containing side chain (S, T, Y), amino acids having a sulfur atom-containing side chain (C, M), amino acids having a carboxylic acid and amide-containing side chain (D, N, E, Q), amino acids having a base-containing side chain (R, K, H), and amino acids having an aromatic compound-containing side chain (H, F, Y, W). Further, it is also known that amino acids are classified by, for example, the mutational matrix (Taylor 1986, J, Theor. Biol. 119, 205-218; Sambrook, J. et al., Molecular Cloning 3rd ed. A7.7-A7.7, Cold Spring Harbor Lab. Press, 2001). Briefly, this classification is as follows: Aliphatic amino acids (L, I, V), aromatic amino acids (H, W, Y, F), charged amino acids (D, E, R, K, H), positively charged amino acids (R, K, H), negatively charged amino acids (D, E), hydrophobic amino acids (H, W, Y, F, M, L, I, V, C, A, G, T, K), polar amino acids (T, S, N, D, E, Q, R, K, H, W, Y), small amino acids (P, V, C, A, G, T, S, N, D), micro amino acids (A, G, S), and large (non-small) amino acids (Q, E, R, K, H, W, Y, F, M, L, I). Note that the letter in parentheses is a one letter amino acid code.

It is already known that a polypeptide having a certain amino acid sequence modified by (i) deletion and/or addition of one or several amino acid residues and/or (ii) substitution of one or several amino acid residues for another amino acid maintains a biological activity of the certain amino acid sequence. Furthermore, the target amino acid residue is more preferably mutated into an amino acid residue having common characteristics to the target amino acid residue as much as possible.

The expression "functionally equal" herein intends that a target protein has biological and biochemical functions equal (identical and/or similar) to those of CLCOL1 protein. Examples of the biological and biochemical functions of CLCOL1 protein herein encompass the function of inducing root elongation and the function of increasing biomass of a plant. Examples of the biological characteristics can encompass a specificity of a site in which a gene encoding CLCOL1 protein is expressed and an amount of the expression.

The gene of the above (c) intends a gene encoding a protein (i.e., the protein of the above (h)) which is a mutant, a derivative, a variant, an allele, a homologue, an ortholog, a partial peptide, or a fusion protein with another protein or another peptide each of which is functionally equal to a protein having the amino acid sequence of SEQ ID NO: 1, the protein having the activity of inducing root elongation of a plant and/or the activity of increasing biomass of a plant. There is no specific limitation on a sequence of the gene of the above (c).

The homology of the amino acid sequence is at least 80% or more, preferably 85% or more, more preferably 90% or more, further more preferably 95% or more, 96% or more, 97% or more, 98% or more, 99% or more, or 99.5% or more to the whole of the amino acid sequence (or to a region of the amino acid sequence which region is necessary to express the function). The homology of the sequence can be determined by the BLASTN program (nucleic acid level) or the BLASTX program (amino acid level) (Altschul et al. J. Mol. Biol., 215: 403-410, 1990). These programs are based on the algorithm BLAST™ by Karlin and Altschul (Proc. Natl. Acad. Sci. USA, 87:2264-2268, 1990, Proc. Natl. Acad. Sci. USA, 90: 5873-5877, 1993). In order to analyze a nucleotide sequence by the BLASTN program, parameters are set so that score=100 and wordlength=12, for example. In order to analyze the amino acid sequence by the BLASTX program, parameters are set so that score=50 and wordlength=3, for example. In order to analyze an amino acid sequence by the Gapped BLAST™ program, the analysis can be carried out as described by Altschul et al. (Nucleic Acids Res. 25: 3389-3402, 1997). In order to carry out analysis by the BLAST™ program and the Gapped BLAST™ program, default parameters of these programs are used. Specific methods for carrying out these analyses are well known. In order to optimally align a control nucleotide sequence or a control amino acid sequence, addition or deletion (e.g., a gap) may be allowed.

The term "homology" as used herein intends a percentage (e.g., homology, positive) of the number of amino acid residues having similar characteristics to the original. However, more preferably, the "homology" is a percentage (identity) of the number of amino acid residues identical to the original. Note that the characteristics of the amino acid are as described above.

As to the gene of the above (d), SEQ ID NO: 2 expresses the nucleotide sequence (ORF) of a gene encoding CLCOL1 protein having the amino acid sequence of SEQ ID NO: 1. The nucleotide sequence of SEQ ID NO: 2 consists of 1014 bases in a total length, and "TAA" indicated at the end is a termination codon.

The gene of the above (e) intends a gene encoding a protein that hybridizes under stringent conditions with a polynucleotide having a nucleotide sequence which is complementary to a nucleotide sequence of any one of the above polynucleotides (a) through (d), the protein having the activity of inducing root elongation of a plant and/or the activity of increasing biomass of a plant.

Since CLCOL1 gene is a key factor relating to root elongation, it is considered that CLCOL1 gene exists in the whole of a wide variety of vascular plants. Namely, the gene of the present invention encompasses homologous genes of CLCOL1 gene existing in various plants. Here, methods which are used to isolate the homologous gene and are well-known to a person skilled in the art encompass a hybridization technique (Southern, E. M., Journal of Molecular Biology, Vol. 98, 503, 1975) and a polymerase chain reaction (PCR) technique (Saiki, R. K., et al. Science, vol. 230, 1350-1354, 1985, Saiki, R. K. et al. Science, vol. 239, 487-491, 1988). Namely, the person skilled in the art can isolate the homologous genes of CLCOL1 gene from various plants by (i) using, as a probe, the whole of or a part of the nucleotide sequence of CLCOL1 gene (e.g., DNA shown in SEQ ID NO: 2) or (ii) using, as a primer, an oligonucleotide that specifically hybridizes with CLCOL1 gene.

Here, the "stringent conditions" refer to conditions under which a double-stranded polynucleotide specific to the nucleotide sequence is formed and a double-stranded polynucleotide not specific to the nucleotide sequence is not formed. In other words, the "stringent conditions" can be expressed as such conditions under which hybridization is carried out at a temperature in a range from (i) a melting temperature (Tm) of nucleic acids having a high homology (e.g., a perfectly-matched hybrid) to (ii) 15° C., preferably 10° C., further preferably 5° C. lower than the melting temperature (Tm). In one example of the stringent conditions, hybridization is carried out in a generally-used hybridization buffer at 68° C. for 20 hours. For example, hybridization is carried out in a buffer (including 0.25M $Na_2HPO_4$, pH7.2, 7% SDS, 1 mM EDTA, 1×Denhardt's solution) for 16 hours through 24 hours at a temperature in a range from 60° C. to 68° C., preferably at 65° C., further preferably at 68° C., and then washing is carried out twice in a buffer (including 20 mM $Na_2HPO_4$, pH7.2, 1% SDS, 1 mM EDTA) for 15 minutes at a temperature in a range from 60° C. to 68° C., preferably at 65° C., further preferably at 68° C. For another example, prehybridization is carried out overnight at 42° C. in a hybridization solution (including 25% formamide or 50% formamide (for a severer condition), 4×SSC (sodium chloride/sodium citrate), 50 mM Hepes pH7.0, 10×Denhardt's solution, 20 µg/ml denaturation salmon sperm DNA), and then hybridization is carried out by adding a labeled probe thereto and keep the resulting solution at 42° C. overnight. In washing following the hybridization, conditions for a washing solution and a temperature are approximately "1×SSC, 0.1% SDS, 37° C.", approximately "0.5× SSC, 0.1% SDS, 42° C." for a severer condition, approximately "0.2×SSC, 0.1% SDS, 65° C." for a further severer condition. As such, as the conditions for the washing following the hybridization become severer, isolation of DNA having a higher homology to the sequence of the probe can be expected. However, the above-indicated combinations of conditions on SSC, SDS, and temperatures are merely examples. The person skilled in the art can provide the same stringency as above by appropriately combining the above-described or other elements that determine stringency of hybridization (for example, other elements include a probe concentration, a probe length, and a time period for a hybridization reaction). For example, the person skilled in the art can easily obtain such a gene by referring to, for example, Molecular Cloning (Sambrook, J. et al., Molecular Cloning: a Laboratory Manual 2nd ed., Cold Spring Harbor Laboratory Press, 10 Skyline Drive Plainview, N.Y. (1989)).

Further, the gene of the above (e) preferably has 80% or more, preferably 85% or more, more preferably 90% or more, further more preferably 95% or more, 96% or more, 97% or more, 98% or more, or 99% or more homology to the sequence of the gene of the above (d) (the nucleotide sequence of SEQ ID NO: 2). The homology to the nucleotide sequence of SEQ ID NO: 2 can be determined by the FASTA search or the BLAST™ search. The nucleotide sequence of the polynucleotide can be determined by the dideoxy method described in Science, 214: 1205 (1981).

Genomic DNA and cDNA can be prepared by means known to the person skilled in the art. As to the genomic DNA, for example, genomic DNA is extracted from a plant, and a genomic library thereof (as a vector, a plasmid, a phage, a cosmid, BAC, PAC, or the like can be used) is prepared. The genomic library is developed, and colony hybridization or plaque hybridization is carried out by use of a probe prepared based on the above gene (for example, the gene shown in SEQ ID NO: 2), so that a clone of the gene is obtained. In this manner, the genomic DNA can be prepared. Alternatively, the genomic DNA can be prepared by preparing a primer specific to the above gene and carrying out PCR with use of the primer. As to the cDNA, for example, cDNA is synthesized based on mRNA extracted from a plant, and the cDNA is inserted into a vector such as λZAP so as to prepare a cDNA library. The cDNA library is developed, and colony hybridization or plaque hybridization is carried out in a similar manner to the above or PCR is carried out. In this manner, the cDNA can be prepared.

The ortholog of the protein having the amino acid sequence of SEQ ID NO: 1 can be, for example, as follows:

SEQ ID NO: 4 shows an amino acid sequence of a homologous protein to CLCOL1 protein in a cultivated watermelon. The protein shown in SEQ ID NO: 4 has an amino acid sequence completely identical to that of CLCOL1 protein. Thus, the protein shown in SEQ ID NO: 4 also has the function of inducing root elongation. As shown in the later-described Examples, the cultivated watermelon is sensitive to dryness as compared with the wild watermelon, and no development in a dry-responsive root system or no increase in expression of the gene are observed in the cultivated watermelon. This difference is assumed to be caused by a difference in a promoter sequence between the cultivated watermelon and the wild watermelon. SEQ ID NO: 5 shows a nucleotide sequence of ORF encoding the protein shown in SEQ ID NO: 4.

SEQ ID NO: 6 shows an amino acid sequence of an ortholog of CLCOL1 protein in a cucumber. The protein shown in SEQ ID NO: 6 is a protein consisting of 337 amino acids, and is a CONSTANS-like transcription factor, too. A homology between the protein of SEQ ID NO: 6 and CLCOL1 protein was analyzed by BLASTN, with the result that a very high homology was found therebetween (Length=1014, Score=639 bits (1649), Expect=0.0, Method: Compositional matrix adjust. Identities=326/337 (96%), Positives=329/337 (97%)). Thus, the protein shown in SEQ ID NO: 6 also has the function relating to root elongation. SEQ ID NO: 7 shows a nucleotide sequence of ORF encoding the protein shown in SEQ ID NO: 6.

Note that an ortholog of CLCOL1 protein exists also in a melon, although a total-length amino acid sequence thereof is unknown. In a published DB of melon unigene (cDNA) (www.icugi.org/cgi-bin/ICuG I/tool/blast.cgi), a homology search for the amino acid sequence of CLCOL1 protein was carried out by use of BLASTN (expect <1e-2), with the result that a sequence having a very high homology to that of CLCOL1 protein was found (DB accession number: MU46046 (Length=719, Score=380 bits (977), Expect(3) =e-112, Method: Compositional matrix adjust. Identities=183/187 (97%), Positives 183/187 (97%)). A presumed-ortholog existing in the melon also has the function relating to root elongation, and is encompassed in the scope of the present invention.

Further, a homology search was carried out in nrDB of NCBI, with the result that a plurality of genes having a high homology to CLCOL1 gene were found. Table 1 shows genes having 60% or more identity and 70% or more homology (positive).

TABLE 1

| | Genbank Accession No. | annotation | % identity | % positives |
|---|---|---|---|---|
| 1 | gi|321146482|gb|ADW65758.1| | CONSTANS- like protein [*Gossypium hirsutum*] | 78.47 | 87.02 |
| 2 | gi|197726026|gb|ACH73166.1| | CONSTANS- like protein [*Prunus persica*] | 75.07 | 84.06 |
| 3 | gi|255548652|ref|XP_002515382.1|; gi|223545326|gb|EEF46831.1| | Salt- tolerance protein, putative [*Ricinus communis*] | 75.73 | 85.38 |
| 4 | gi|4091806|gb|AAC99310.1|; gi|189014384|gb|ACD69428.1|; gi|302398739|gb|ADL36664.1| | CONSTANS- like protein 2 [*Malus × domestica*] | 71.26 | 82.7 |
| 5 | gi|189014382|gb|ACD69427.1| | CONSTANS- like 1 [*Malus × domestica*] | 72.46 | 82.32 |
| 6 | gi|224760941|gb|ACN62415.1| | CONSTANS- like protein [*Mangifera indica*] | 70.43 | 79.71 |
| 7 | gi|4091804|gb|AAC99309.1| | CONSTANS- like protein 1 [*Malus × domestica*] | 71.59 | 81.45 |
| 8 | gi|225430571|ref|XP_002263458.1| | PREDICTED: hypothetical protein [*Vitis vinifera*] | 71.92 | 79.08 |
| 9 | gi|118489345|gb|ABK96477.1| | unknown [*Populus trichocarpa × Populus deltoides*] | 69.3 | 79.44 |
| 10 | gi|224143378|ref|XP_002324936.1|; gi|222866370|gb|EEF03501.1| | predicted protein [*Populus trichocarpa*] | 69.01 | 78.87 |
| 11 | gi|224092663|ref|XP_002309695.1|; gi|222855671|gb|EEE93218.1| | predicted protein [*Populus trichocarpa*] | 69.77 | 79.66 |
| 12 | gi|52840166|sp|Q940T9.2|COL4_ARATH; gi|225898929|dbj|BAH30595.1| | RecName: Full = Zinc finger protein CONSTANS- LIKE 4 [*Arabidopsis thaliana*] | 63.49 | 74.93 |
| 13 | gi|30689668|ref|NP_197875.2| GENE ID: 832563 AT5G24930 | zinc finger (B- box type) family protein [*Arabidopsis thaliana*] | 63.49 | 74.93 |
| 14 | gi|297808501|ref|XP_002872134.1|; gi|297317971|gb|EFH48393.1| | hypothetical protein ARALYDRAFT_489353 [*Arabidopsis lyrata* subsp. *lyrata*] | 63.11 | 74.86 |
| 15 | gi|296082181|emb|CBI21186.3| | unnamed protein product [*Vitis vinifera*] | 63.79 | 71.26 |

As shown in Table 1, genes having a high homology to the gene of the present invention exist in a wide variety of plants such as dicotyledons, conifers (e.g., *Picea likiangensis* and *Pinus radiata*), and bryophytes (e.g., *Physcomitrella patens*). No monocotyledon is shown in Table 1; however, a rice gene having a sequence analogous to the sequence of CLCOL1 gene of the present invention has been reported (Mol. Cells, Vol. 17, No. 1, pp. 10-16).

The gene of the present invention can be obtained by a conventionally-conducted polynucleotide modification method. Namely, by substitution, deletion, insertion, and/or addition of a certain base of a polynucleotide having genetic information of a protein, it is possible to produce a polynucleotide having genetic information of a desired recombinant protein. A specific method for modifying the base of the polynucleotide can be (i) any known method such as the Kunkel method or the Gapped duplex method or (ii) any method corresponding thereto. The method therefor can be, for example, use of any of commercially-available kits for mutagenesis utilizing the site-directed mutagenesis (e.g., Mutant-K and Mutant-G (each of which is a product name and is available from TAKARA Bio Inc.), KOD-Plus Site-Directed Mutagenesis Kit (available from Toyobo Co., Ltd.), Transformer Site-Directed Mutagenesis Kit (available from Clontech), and QuickChange Site Directed Mutagenesis Kit (available from Stratagene)). Alternatively, the method utilizing the polymerase chain reaction (PCR), e.g., a method involving use of LA PCR in vitro Mutagenesis series kit (product name, available from TAKARA Bio Inc.), may be employed. A method for the mutagenesis can be (i) a method involving use of a chemical mutagen as typified by EMS (ethyl methanesulfonate), 5-bromouracil, 2-aminopurine, hydroxylamine, N-methyl-N'-nitro-N-nitrosoguanidine, or other carcinogenic compound, or (ii) a method of carrying out a treatment with a radiation as typified by an X-ray, an alpha ray, a beta ray, a gamma ray, or an ion beam or an ultraviolet treatment. These methods are known to the person skilled in the art.

The gene used in the present invention may be a gene consisting only of the polynucleotide encoding the above protein, or may be a gene having the polynucleotide encoding the above protein and an additional nucleotide sequence. The additional nucleotide sequence is not particularly limited, and may be, for example, a nucleotide sequence encoding a label (e.g., a histidine tag, a Myc tag, or a FLAG tag), a fusion protein (e.g., streptavidin, cytochrome, GST, GFP, or MBP), a promoter sequence, or a signal sequence (e.g., an endoplasmic reticulum localization signal sequence or a secretory sequence). A site in which such the nucleotide sequence is added is not particularly limited, and may be, for example, the N-terminal or the C-terminal of the protein to be translated.

<2. Recombinant Expression Vector>

The present invention provides a recombinant expression vector including the above gene. The recombinant expression vector of the present invention can be a vector for expressing the gene of the present invention in a host cell in order to produce a transformant, or can be the one used to produce a recombinant protein. An organism which is to be transformed is not particularly limited, and may be, for example, a bacterium, an insect, an animal, or a plant. Particularly preferably, the organism which is to be transformed is a plant.

In the present invention, as a vector from which the recombinant expression vector is prepared, any of various conventionally-known vectors can be used. Such the vector can be, for example, a plasmid, a phage, or a cosmid. Of these, a suitable one can be selected according to a plant cell to which the vector is to be introduced or a method of the introduction. Specifically, for example, it is possible to use any of pBluescript vectors, pBI vectors, and pUC vectors. Examples of the pBluescript vectors encompass pBluescript SK(+), pBluescript SK(−), pBluescript II KS(+), pBluescript II KS(−), pBluescript II SK(+), and pBluescript II SK(−). Examples of the pBI vectors encompass pBI121, pBI101, pBI101.2, pBI101.3, and pBI221. Binary vectors such as the pBluescript vectors and the pBI vectors are preferable, since each of them can introduce target DNA into a plant via *Agrobacterium*. Examples of the pUC vectors encompass pUC19 and pUC119. The pUC vector is preferable, since the pUC vector can directly introduce DNA into a plant.

The above vector preferably includes (i) a promoter sequence which can be transcribed in a plant cell and (ii) a transcription terminator sequence including a polyadenylation site which is necessary for stabilizing a transcription product. The person skilled in the art can appropriately select such the promoter and transcription terminator sequence. For example, it is possible to use (i) a promoter for constantly expressing a gene in a plant cell or (ii) a promoter for inductively expressing a gene by an external stimulation.

Examples of the promoter for constantly expressing a gene encompass a cauliflower mosaic virus 35S (CaMV35S) promoter (Odell et al. 1985 Nature 313:810), a rice actin promoter (Zhang et al. 1991 Plant Cell 3:1155), a corn ubiquitin promoter (Cornejo et al. 1993 Plant Mol. Biol. 23:567), a nopaline synthetase gene promoter, a tomato ribulose-1.5-bisphosphate carboxylase/oxidase small subunit gene promoter, a napin gene promoter, and an oleosin gene promoter. Among these, the CaMV35S promoter can be more preferably used.

Examples of the promoter for inductively expressing a gene encompass, in addition to those used in the later-described Examples, promoters known to express a gene by an external factor such as infection with/intrusion of a filamentous fungus, a bacterium, or a virus, a low temperature, a high temperature, drying, irradiation of an ultraviolet ray, or scattering of a certain compound. Examples of such the promoter encompass: a promoter of a rice chitinase gene (Xu et al. 1996 Plant Mol. Biol. 30:387) and a promoter of a tobacco PR protein gene (Ohshima et al. 1990 Plant Cell 2:95), each of which genes is expressed by infection with/intrusion of a filamentous fungus, a bacterium, or a virus; a promoter of rice "lip19" gene (Aguan et al. 1993 Mol. Gen. Genet. 240:1), which is induced by a low temperature; promoters of rice "hsp80" gene and "hsp72" gene (Van Breusegem et al. 1994 Planta 193:57), each of which genes is induced by a high temperature; a promoter of *Arabidopsis thaliana* "rab 16" gene (Nundy et al. 1990 Proc. Natl. Acad. Sci. USA 87:1406), which is induced by drying; a promoter of a parsley chalcone synthetase gene (Schulze-Lefert et al. 1989 EMBO J. 8:651), which is induced by irradiation of an ultraviolet ray; a promoter of a corn alcohol dehydrogenase gene (Walker et al. 1987 Proc. Natl. Acad. Sci. USA 84:6624), which is induced under anaerobic conditions; and a promoter which is induced by salt stress (Shinozaki, K. and Yamaguchi-Shinozaki, K., Curr. Opin. Plant Biol. 3, 217-223 (2000)). Each of the promoter of the rice chitinase gene and the promoter of the tobacco PR protein gene is also induced by a certain compound such as a salicylic acid, and "rab 16" is also induced by scattering of an abscisic acid, which is a plant hormone.

In the present invention, in order to promote root elongation, a promoter which expresses a gene in a root tissue can be preferably used. However, the present invention is not limited to this. A preferable example of such the promoter is a drought stress-specific promoter according to the present invention (described in detail later in <6>).

Thus, the present invention also provides a construct including the gene of the present invention to which a suitable promoter is operably linked. Based on the descriptions of the present specification and technical common knowledge, the person skilled in the art can select a suitable promoter appropriately.

Namely, the present invention also encompasses an expression cassette including the above gene of <1> which is linked to the promoter of <6> (described later) (if necessary, the later-described transcription terminator or the like may be linked thereto). This expression cassette can be used as a construct for increasing expression of the above gene. In constructing the expression cassette, for example, cutting sites of DNA segments are made to be protruded terminals which are complementary to each other, and are reacted with each other by a ligation enzyme, so that the order of the DNA segments can be defined. In a case where the expression cassette includes a terminator, the promoter, the above gene, and the terminator may be aligned in this order from the upstream side.

By introducing this expression cassette into an appropriately selected vector from which a recombinant vector of the present invention is prepared, it is possible to provide the recombinant vector of the present invention. There is no particular limitation to reagents for constructing the expression vector, that is, to the types of, e.g., a restriction enzyme and a ligation enzyme. Any of commercially-available ones may be selected and used as appropriate.

There is no particular limitation to the transcription terminator sequence, as long as the transcription terminator sequence has a function as a transcription termination site. The transcription terminator sequence may be any known one. Suitably used as the transcription terminator sequence may be, for example, a transcription termination region (Nos terminator) of a nopaline synthetase gene or a transcription termination region (CaMV35S terminator) of cauliflower mosaic virus 35S. Providing the transcription terminator sequence at a suitable position in the recombinant expression vector makes it possible to prevent (i) an unnecessarily long transcript from being synthesized after the recombinant expression vector is introduced into a plant cell and (ii) the number of copies of a plasmid from being reduced due to a strong promoter.

Further, the recombinant expression vector may include further another DNA segment. There is no particular limitation to such another DNA segment, examples of which encompass a transformant selection marker, an enhancer, and a nucleotide sequence for increasing a translation rate. Furthermore, the recombinant expression vector may further include a T-DNA region. The T-DNA region can increase a gene introduction efficiency particularly in a case where the recombinant expression vector is introduced into a plant body by using *Agrobacterium*.

As the transformant selection marker, a drug resistance gene can be used, for example. Specific examples of the drug resistance gene encompass drug resistance genes against hygromycin, bleomycin, kanamycin, gentamicin, and chloramphenicol (a neomycin phosphotransferase gene having resistance to kanamycin or gentamicin, each of which is an antibiotic, and a hygromycin phosphotransferase gene having resistance to hygromycin). In addition to these, an acetyltransferase gene having resistance to phosphinothricin, which is an herbicide, can be also used, for example. With this, it is possible to easily select a transformed plant body by selecting a plant body living in a medium containing the antibiotic or the herbicide.

As the nucleotide sequence for increasing a translation rate, an omega sequence derived from tobacco mosaic virus can be used, for example. By providing the omega sequence in an untranslated region (5' UTR) of the promoter, it is possible to increase a translation rate of the above fused gene.

As the enhancer, an enhancer region including an upstream sequence of the CaMV35S promoter can be used, for example. Thus, according to the purpose, it is possible to incorporate any of various DNA segments into the recombinant expression vector.

There is no particular limitation to a method of constructing the recombinant expression vector. The recombinant expression vector only needs to be constructed so that the promoter, the gene, the terminator sequence, and another DNA segment as those exemplified above (if necessary) are introduced, in a predetermined order, into an appropriately selected vector from which the recombinant expression vector is prepared. Insertion of the gene into the vector from which the recombinant expression vector is prepared is carried out by a generally-conducted method, for example, such a method in which DNA of a purified gene is cut out by a suitable restriction enzyme and a piece of the DNA thus cut out is inserted into a restriction enzyme site or a multicloning site of a suitable vector DNA (e.g., see Molecular Cloning, 5.51-5.53).

The person skilled in the art can prepare a vector having a desired gene by a general genetic engineering technique as appropriate. Typically, it is possible to prepare such the vector by using any of various commercially-available vectors.

<3. Transformant>

The present invention encompasses a transformant produced by introduction of the above gene or the above recombinant expression vector. Typically, the gene is supported by (inserted into) a suitable vector, which is then introduced into a host cell being a target to be transformed. Namely, the present invention provides a host cell (transformant) retaining the above gene or the above recombinant expression vector.

There is no particular limitation to the host cell, and any of various host cells is used according to the purpose. Examples of a cell in which the gene is to be expressed encompass bacterium cells (e.g., *streptococcus, staphylococcus, E. coli, streptomyces*, and hay *bacillus*), insect cells (e.g., *Drosophila* S2 and *Spodoptera* SF9), animal cells (e.g., CHO, COS, HeLa, C127, 3T3, BHK, HEK293, and Bowes melanoma cell), and plant cells. Since the gene of the present invention is derived from a plant, a plant cell is particularly preferable as a host. Examples of the plant cell encompass various forms of plant cells such as suspension cultured cells, protoplasts, and cells in a plant body. Examples of the transformant of the present invention encompass not only the plant cells but also an entire plant body, plant organs (e.g., a root, a stem, a leaf, a petal, a seed, and a fruit), plant tissues (e.g., epidermis, phloem, parenchyma, xylem, and a vascular bundle), slices thereof, calli, shoot primordia, multiple shoots, hairy roots, and cultured roots.

A method of expressing the above gene in the host cell may be, for example, such a method that the gene is incorporated into a suitable vector and introduced into a living body by a method known to the person skilled in the art, e.g., the polyethylene glycol method, the *Agrobacterium* method, the liposome method, the cationic liposome method, the calcium phosphate precipitation method, the electroporation (Current protocols in Molecular Biology edit. Ausubel et al. (1987) Publish. John Wiley 86 Sons. Section 9.9-9.9), the lipofection method (available from GIBCO-BRL), the microinjection method, or the particle gun method.

The introduction of the gene may be conducted either ex vivo or in vivo. The introduction of the gene of the present invention into a plant body may be carried out by directly introducing the gene into a plant cell by, e.g., the microinjection method, the electroporation method, or the polyethylene glycol method. Alternatively, the introduction can be carried out by indirectly introducing the gene into a plant cell with use of a vector prepared by introducing the gene into a plasmid for introducing the gene into the plant, i.e., via a virus or a bacterium each of which has an ability to infect a plant. Examples of the virus encompass, as representative viruses, a cauliflower mosaic virus, a tobacco mosaic virus, and a geminivirus. Examples of the bacterium encompass *Agrobacterium*. Introduction of the gene into a plant by the *Agrobacterium* method can be carried out with use of a commercially-available plasmid. A method of introducing the gene of the present invention into a plant body with use of such the vector is preferably the leaf desk method of carrying out gene introduction via *Agrobacterium* (Jorgensen, R. A. et al., (1996). Chalcone synthase cosuppression phenotypes in petunia flowers: comparison of sense vs. antisense constructs and single-copy vs. complex T-DNA sequences. Plant Mol. Biol. 31, 957-973.).

The "plant" which is a target to be transformed in the present invention is not particularly limited, as long as the plant is a vascular plant having a root. Preferably, the plant is angiosperms, and may be either of a monocotyledon and a dicotyledon. Further, examples of the plant can encompass not only herbaceous plants but also woody plants.

Examples of the "monocotyledon" encompass: Orchidaceae (e.g., *Cymbidium goeringii* and vanilla), Poaceae (e.g., rice, wheat, barley, rye, corn, common millet, foxtail millet, and sugar cane), Cyperaceae (e.g., a papyrus and *Eleocharis dulcis*), Araceae (e.g., a taro, a cocoyam, and *Colocasia gigantea*), Alismataceae (e.g., an arrowhead), Liliaceae (e.g., a leek, a shallot, an onion, a Japanese scallion, a Welsh onion, a cibol, a garlic, chives, a Chinese chive, an asparagus, a golden-rayed lily, a tiger lily, and a Maxmowicz's lily (three kinds of lily bulbs)), Dioscoreaceae (e.g., a water yam, a yam (a Chinese yam and a cinnamon vine)), and a Japanese yam), Zingiberaceae (e.g., a myoga ginger and a ginger), and, as the woody plants, bamboo (e.g., a madake bamboo, a henon bamboo, and a moso bamboo) and a palm.

The "dicotyledon" may be either of a choripetalous flower and a gamopetalous flower. Examples of the dicotyledon encompass: Asteraceae (e.g., a sunflower, a lettuce, a burdock, a garland chrysanthemum, an edible chrysanthemum, an endive, a chicory, *Cirsium dipsacolepis* (a pokeweed), an artichoke (*Cynara scolymus*), a Japanese silverleaf, *Gynura bicolor*, a Jerusalem artichoke, *Lactuca sativa*, a romaine lettuce, a Japanese butterbur, a viper's grass, a dandelion, and a salsify (*Tragopogon porrifolius*)), Fabaceae (e.g., a soybean, a pea, a fava bean, a peanut, a sword bean, a hyacinth bean, a runner bean, a lima bean, a kidney bean, a Yokohama bean, *Vicia unijuga*, a mung bean, and a cowpea), Rubiaceae (e.g., a coffee bean), Lamiaceae (e.g., a *perilla*, a sage, a chorogi, a thyme, a wild sesame, and a Japanese mint), Euphorbiaceae (e.g., a castor-oil plant and a cassava), Melastomataceae, Myrtaceae (e.g., a rose apple), Apocynaceae, Malvaceae (e.g., an okra), Ericaceae, Gesneriaceae, Apiaceae (e.g., a carrot, a parsley, a celery, *Angelica keiskei*, a celery, a coentro, a honewort, a fennel, *Glehnia littoralis*, a dropwort, and a parsnip), Brassicaceae (e.g., a rapeseed, a Japanese radish, horseradish, a Chinese mustard (taisai, shakushina), a potherb mustard, *Brassica narinosa*, a colza, a Chinese cabbage, a turnip, *Brassica juncea* Czern. et Coss (daishinsai), an Indian mustard, a leaf mustard, *Brassica juncea* Czern. et Coss (tanikutakana), a kale, a Chinese kale, a cauliflower, a cabbage, Brussels sprouts, a kohlrabi, a broccoli, a rutabaga, *Brassica×napus*, a wasabi, a radish, and a watercress), Acanthaceae, Rosaceae (e.g., an apple, a cherry, and a strawberry), Boraginaceae, Urticaceae, Ranunculaceae, Solanaceae (e.g., a potate, a tomato, a red pepper, a tobacco, a green pepper, and an eggplant), Polygonaceae (e.g., a water pepper (*Persicaria hydropiper*), *Persicaria tinctoria*, and a rhubarb, Chenopodiaceae (e.g., a Swiss chard, a table beet (beetroot), a summer cypress, *Salsola komarovii*, a spinach, and a sea blite), Amaranthaceae (e.g., an edible *amaranthus*), Molluginaceae (e.g., a New Zealand spinach (*Tetragonia tetragonoides*)), Portulacaceae (e.g., a kitchen garden (*Portulaca oleracea* L.)), Basellaceae (e.g., an Indian spinach), Nymphaeaceae (e.g., a watershield and a lotus (lotus root)), Rutaceae (e.g., a prickly ash), Onagraceae (e.g., a water chestnut), Araliaceae (e.g., an udo and a Japanese angelica-tree), Convolvulaceae (e.g., a swamp morning glory and a sweet potato), Cucurbitaceae (e.g., a wax gourd, a watermelon, a melon cucumber, an Oriental melon, a melon, a cucumber, a pumpkin/squash (three kinds: *C. moschata, C. maxima*, and *C. pepo*), a moonflower, a loofah, a balsam pear (a bitter cucumber), and a chayote), and, as the woody plants, a camphor tree, *Castanopsis cuspidata*, a cherry tree, an azalea, and a honeysuckle.

Note that the method of the transformation is preferably selected according to the type (e.g., the monocotyledon or the dicotyledon) of a plant or the like serving as a host, as appropriate.

The present invention encompasses not only a host cell into which the above gene or the above vector is directly introduced but also, in cases where the host cell is of a higher plant for example, a plant body grown from a plant cell, a plant which is a progeny, an offspring, or a clone of that plant, and a breeding material (e.g., a seed, a fruit, a cut ear, a tuber, a tuberous root, a stock, a callus, and a protoplast). Reproduction of a plant body from a transformed plant cell can be carried out by a method known to the person skilled in the art, according to the type of the plant cell. For example, a method of producing a transformed plant body may be, but is not limited to, a method of reproducing a plant body by introducing a gene into a protoplast by polyethylene glycol, a method of reproducing a plant body by introducing a gene into a protoplast by an electrical pulse, a method of reproducing a plant body by directly introducing a gene into a cell by the particle gun method, and a method of reproducing a plant body by introducing a gene via *Agrobacterium*. These techniques have been already established, and have been widely used in the technical filed of the present invention. Any of these techniques can suitably be used in the present invention.

An applicable method of reproducing a plant body by redifferntiation of a transformed plant cell varies according to the type of the plant cell. In a case where the plant cell is of rice, a method by Fujimura et al. (Plant Tissue Culture Lett. 2:74 (1995)) is applicable. In a case where the plant cell is of corn, a method by Shillito et al. (Bio/Technology 7:581 (1989)) or a method by Gorden-Kamm et al. (Plant Cell 2:603 (1990)) is applicable. After a foreign gene is introduced into a transformed plant body which is reproduced by any of the above methods and has been grown, it is possible to determine whether or not the foreign gene exists in the plant body by a known technique such as PCR or the Southern hybridization method or by analyzing a nucleotide sequence of DNA in the plant body. In this case, extraction of DNA from the transformed plant body can be carried out according to a known method by J. Sambrook et al. (Molecular Cloning, second edition, Cold Spring Harbor Laboratory Press, 1989).

For example, in order to assay, by PCR, the gene of the present invention existing in a reproduced plant body, an amplification reaction is carried out by using, as a template, DNA extracted from the reproduced plant body by the above-described method. Alternatively, the amplification reaction can be carried out in a reaction solution in which primers are mixed, the primers being synthesized oligonucleotides having nucleotide sequences suitably selected according to a nucleotide sequence of the gene of the present invention or a modified gene of the present invention. During the amplification reaction, repeatedly carrying out a cycle of denaturation, annealing, and elongation of DNA some dozen times gives amplification products of DNA fragments each including the nucleotide sequence of the gene of the present invention. By subjecting the reaction solution containing the amplification products to, for example, agarose electrophoresis, the various DNA fragments thus amplified are fractionated. Among these, it is possible to find a DNA fragment corresponding to the gene of the present invention.

Once a transformed plant body having a genome into which the gene of the present invention is introduced is obtained, it is possible to obtain its offspring by sexual reproduction or asexual reproduction of the plant body. Further, it is also possible to mass-produce the plant body from a breeding material obtained from the plant body, an offspring thereof, or a clone thereof. The present invention encompasses a plant cell into which the gene or the recombinant expression vector of the present invention is introduced, a plant body including the plant cell, an offspring and a clone of the plant body, and a breeding material of the plant body, an offspring thereof, or a clone thereof. Namely, the present invention encompasses (i) a "T0 generation", which is a first redifferntiation generation in which transformation is carried out, (ii) a progeny plant such as a "T1 generation", which is obtained by self-fertilization of the T0-generation plant, and (iii) a hybrid plant obtained by cross-fertilization with use of, as one parent, the T0-generation plant or the T1-generation plant and a progeny plant of the hybrid plant.

A plant body produced in this manner has a root system whose development is promoted and/or has an increased biomass, as compared with a general plant. Therefore, such the plant body is very useful.

Further, the present invention can encompass a method for producing a plant body, including the steps of: preparing plants in each of which expression of the gene of <1> above is increased; and measuring (i) root elongation and/or (ii) biomass of each of progeny plants of the plants and, among the progeny plants, selecting a line in which (i) the root elongation and/or (ii) the biomass is significantly improved. The "plants in each of which expression of the gene of the above <1> is increased" are preferably, but are not limited to, transformed plants. From such the plants, it is possible to obtain progeny plants according to an established manner. By selecting a progeny plant maintaining a trait of overexpressing the above gene based on (i) the root elongation and/or (ii) the biomass, it is possible to produce a stable plant line whose biomass is increased thanks to the above trait.

Further, it is also possible to obtain a breeding material (e.g., a plant cell, a seed, a fruit, a stock, a callus, a tuber, a cut ear, or a tuberous root) from such the plant or its offspring, so as to mass-produce, from the breeding material, stable plant lines whose (i) root elongation and/or (ii) biomass is improved.

<4. Plant in which Root Elongation is Induced or Whose Biomass is Increased and Method for Producing Such Plant>

The present invention encompasses not only the above transformant but also a method for producing the transformant. Particularly, the present invention encompasses a method for producing (breeding) a plant in which root elongation is induced or whose biomass is increased, including the step of: increasing, in a plant, expression of the gene of the present invention. Other embodiments of this method only need to include the step of increasing, in a plant, expression of the gene of the present invention, and there is no particular limitation to other step(s), condition(s), material(s), and the like. For a plant or the like which is a target of this method, the descriptions in the above <3> are quoted as references as appropriate.

Further, the present invention encompasses not only the transformed plant but also a plant in which expression of the above gene is increased so that its root elongation is induced and/or its biomass is increased. A control for comparison of the increase may be, for example, a wild plant. The plant in which expression of the gene is increased only needs to have the above-described trait, and may be produced by any method such as transformation, mutation, or conventional breeding.

By the "increasing expression of the gene", it is only necessary that an expression level (production amount) of a protein encoded by the above gene is increased in a target plant. The increasing may be achieved by transducing an external gene or by increasing an expression level of an endogenous gene. A degree of the increasing is also not particularly limited. By the increasing, it is only necessary that the plant in which expression of the gene is increased consequently represents a phenotype in which root elongation is promoted or its biomass is increased as compared with a control plant (e.g., a plant into which the gene is not introduced or a wild plant). As in the later-described Examples, (i) whether or not the root elongation is promoted or (ii) whether or not the biomass is increased can easily be evaluated by measuring a dry weight of a root of the plant or other biomass (e.g., a culm length of the plant, a maximum ear length of the plant, and/or a total ear weight of the plant).

As a method for increasing the expression level of the endogenous gene, for example, a mutagenesis technique can be used. For example, genes of target plants may be mutated either by use of (i) a chemical mutagen as typified by EMS (ethyl methanesulfonate), 5-bromouracil, 2-aminopurine, hydroxylamine, N-methyl-N'-nitro-N-nitrosoguanidine, or other carcinogenic compound or (ii) a treatment with an irradiation as typified by an X-ray, an alpha ray, a beta ray, a gamma ray, or an ion beam or an ultraviolet treatment. Then, among the resulting plants, a strain in which expression of the above gene is increased may be selected. These methods are known to the person skilled in the art.

The external gene can be transduced by a conventionally-known genetic engineering technique. Specifically, the transduction can be carried out by use of the above-described recombinant expression vector or any of the various methods explained in <3>. Namely, the method for producing the transformant preferably includes the step of producing a transformed plant cell by introducing, into a plant cell, the above gene or the above recombinant expression vector. Note that, in the present invention, examples of a plant material which is to be transformed encompass plant tissues (such as a root, a stem, a leaf, a seed, a mature embryo, an immature embryo, an ovule, an ovary, a shoot apex, an anther, and a pollen), slices thereof, cells, calli, and plant cells such as a protoplast obtained from a cell that had a cell wall removed with an enzyme treatment.

Further, the method for producing the transformant preferably includes the step of reproducing a plant body from the transformed plant cell. The plant cell transformed in the above-described manner can be reproduced into an organ or a plant individual by a tissue culture method known to the person skilled in the art. Such the method can be, for example, a method in which callus-like transformed cells are transferred to a medium containing a different kind of hormone with a different concentration and are cultured therein, so that an adventive embryo is formed, from which a complete plant body is obtained. Specific example thereof is as follows: First, in a case where the plant material which is to be transformed is a plant tissue or a protoplast, the plant material is cultured in a callus forming medium which is prepared by sterilization after addition of substances such as a mineral element, a vitamin, a carbon source, a saccharide serving as an energy source, and a plant growth-regulating substance (a plant hormone such as auxin and/or cytokinin), so that a dedifferentiated callus proliferated in an indefinite form is formed (hereinafter, referred to as "callus induction"). The callus thus formed is transferred to a new medium containing a plant growth-regulating substance such as auxin, and then is further proliferated (subculture). Here, the callus induction can be carried out efficiently and in a large quantity with a solid medium such as agar, whereas the subculture can be carried out efficiently and in a large quantity with, e.g., a liquid medium. Next, the callus proliferated by the subculture is cultured under suitable conditions, so that redifferntiation of an organ is induced (hereinafter, referred to as "redifferntiation induction"). Consequently, a complete plant body is reproduced. The redifferntiation induction can be carried out by appropriately setting, e.g., (i) kinds and amounts of various components in the medium (e.g., a plant growth-regulating substance such as auxin and/or cytokinin, and a carbon source), (ii) light, and (iii) a temperature. As a result of the redifferntiation induction, an adventitious embryo, an adventitious root, an adventitious bud, an adventitious stem and leaf, and/or the like is formed, which is then grown into a complete plant body. Alternatively, the one which is not grown to a complete plant body yet may be put in storage or the like (e.g., in the form of a synthetic seed which is encapsulated, a dried embryo, a freeze-dried cell, or a freeze-dried tissue).

For another example, in a case where the plant material to be transformed is a plant tissue, e.g., a leaf disc, the leaf disc is infected with *Agrobacterium*, and then is cultured under suitable light and temperature conditions on a redifferntiation solid medium which is prepared by sterilization after addition of substances such as a mineral salt, a vitamin, a carbon source (e.g., a saccharide serving as an energy source), a plant growth-regulating substance (e.g., a plant hormone such as auxin and/or cytokinin), and a selection reagent (e.g., kanamycin), so that a stem and a leaf are formed. Next, the stem and leaf are cultured on a medium (rooting medium) prepared by removing the plant growth-regulating substance from the above solid medium, so that an adventitious root is induced. A complete plant body is reproduced therefrom. The medium used therefor may be, for example, any of generally-used ones such as an LS medium and an MS medium.

A plant body of the present invention in which root elongation is induced or whose biomass is increased can be produced also by a breeding method. Examples of the breeding method encompass a general breeding method (e.g., a crossbreeding method) of carrying out crossbreeding a plant with a breed having the gene of the present invention. By such the method, it is possible to produce the plant body in which root elongation is induced or whose biomass is increased. The production of the plant body of the present invention by the breeding method can be appropriately carried out by referring to various publicly-known literatures (Saibou Kougaku Bessatsu (Cell Technology Extra Number), Shokubutsu Saibou Kougaku (Plant Cell Technology) Series 15, "Model Shokubutsu no Jikken Protocol (Experimental Protocol of Model Plant)", Shujunsha, 2001).

A preferable mode of the breeding method is, for example, a method including the steps of: (i) producing a plant of a breed by crossbreeding (a) a plant in which root elongation is induced or whose biomass is increased with (b) a plant having a given function; and (ii) determining whether or not the root elongation is promoted or the biomass is increased in the plant produced in the step (i). Another mode of the breeding method is, for example, a method including the steps of: (i) crossbreeding a plant with a plant having the gene of the present invention and (ii) selecting a modified plant body having the gene.

Further another mode of the breeding method is, for example, a method including the steps of: (A) producing F1 by crossbreeding Plant A with Plant B having the gene of the present invention; (B) crossbreeding the F1 with the Plant A; (C) selecting a plant having the gene; and (D) crossbreeding the plant selected in the step (C) and the Plant A.

In this method, "backcrossing" is carried out by (i) crossbreeding the Plant B, which has the gene of the present invention, with a plant (referred to as "Plant A") in which root elongation is to be induced, (ii) selecting an individual which inherits the gene of the present invention included in the Plant B and which is close to the Plant A, and (iii) crossbreeding the selected individual with the Plant A again. By such the backcrossing, the trait of the gene of the present invention included in the Plant B is intentionally introduced into the Plant A. In this method, by selecting the plant having the gene of the present invention with use of a DNA marker that is typically used in genome breeding according to a conventional technique, it is possible to efficiently carry out substitution by the "backcrossing". This shortens a breeding period, and makes it possible to accurately prevent an extra genome region from being mixed therein. Typically, the "backcrossing" may cause such a problem that a trait of another gene strongly linked to the gene of the present invention cannot be eliminated by any means. However, by using the DNA marker existing in the vicinity of the gene of the present invention, it is possible to accurately select a desired plant. The same applies to the method for obtaining a plant whose biomass is increased.

The above method can be repeatedly carried out as needed until an entire genome region except for that of the gene of the present invention is fixed to have a target genetic trait in a homo state. Namely, from among the individuals obtained by crossbreeding in the step (D), a plant individual having the gene of the present invention and having a genomic structure close to that of the Plant A can be selected with use of a generally-used DNA marker. Further, the selected plant individual can be "backcrossed" (i.e., crossbred with the Plant A) as needed.

Particularly by the genome breeding method involving use of the DNA marker, subsequent breeding can be carried out with a selected individual having a high substitution rate. Therefore, selection efficiency becomes better at later generations. Further, this method handles only a small number of individuals, and therefore makes it possible to carry out the breeding in a small space. Furthermore, this method makes it possible to carry out the crossbreeding plural times in a year by using a greenhouse or an air-conditioned room.

The selecting the plant with use of the DNA marker in the step (C) intends selecting the plant based on information of a base type of a nucleotide sequence (e.g., polymorphism) characterizing that DNA marker. For example, in a case where a polymorphic modification exists in the vicinity of the gene of the present invention, the selecting the plant with use of the DNA marker means selecting an individual having the same polymorphic variation as that existing in the vicinity of the gene of the present invention. Thus, the above breeding method can also be called a "genome breeding" method preferably using a DNA marker. In other words, the "genome breeding" is a "marker breeding". The DNA marker available in the above breeding method is not particularly limited, and any of various generally-known DNA markers can be suitably used. Examples of such the DNA markers encompass a RFLP (restriction fragment length polymorphism) marker, an SSR (simple sequence repeat) marker, and an SNP (single nucleotide polymorphism) marker.

Note that increasing expression of the gene of the present invention so as to induce root elongation or to increase biomass is applicable not only to dicotyledons such as a watermelon and *Arabidopsis thaliana* but also to a wide variety of general vascular plants, particularly to monocotyledons. A gene similar to (i.e., a gene having a high sequence homology with) the watermelon-derived gene which was confirmed in the present invention to be effective exists, of course, in the dicotyledons even except for Cucurbitaceae and *Arabidopsis thaliana*. Not only this, such the homologous gene exists also in a wide variety of monocotyledons. Particularly noteworthy, such the homologous gene exists also in rice, which is distantly related to the watermelon and *Arabidopsis thaliana* from the standpoint of taxology (Mol. Cells, Vol. 17, No. 1, pp. 10-16). Namely, the homologous gene of the above-described gene of the present invention exists not only in the dicotyledons but also in a wide variety of general vascular plants including the monocotyledons. From the fact that the gene is preserved in a wide variety of plants ranging from the dicotyledons to the monocotyledons, it is highly possible that the dicotyledons and the monocotyledons share a common root elongating mechanism or a common biomass increasing mechanism due to the gene of the present invention.

Reading the present specification in consideration of the above-described points, the person skilled in the art would understand that introducing the above-described gene of the present invention into a plant and increasing expressing of the gene therein makes it possible to promote root elongation in the plant or to increase biomass of the plant, even if the plant is not a dicotyledon. For example, it is possible to apply the present invention to a monocotyledon merely by replacing a plant material (dicotyledon) used in the later-described Examples with the monocotyledon. In such the case, it is known to the person skilled in the art that, e.g., an experimental procedure(s) and/or a material(s) may be changed as needed in consideration of technical standards and technical common knowledge at the time of filing of the present application.

Further, the present invention can encompass a method for inducing root elongation of a plant, including the step of increasing expression of the above gene. Furthermore, the present invention encompasses a method for increasing biomass of a plant, including the step of increasing expression of the above gene. The step of increasing expression of the gene can be suitably carried out by using any of the above-described methods.

<5. Agent for Inducing Root Elongation of Plant or Increasing Biomass of Plant>

The present invention also encompasses an agent including, as an active element, the above gene or the above recombinant expression vector, the agent inducing root elongation of a plant or increasing biomass of a plant (hereinafter, such the agent is collectively referred to as an "elongation induction agent or the like"). The elongation induction agent or the like is applied to a plant, and is provided as a composite containing a carrier element acceptable to a publicly-known agent (e.g., a plant growth regulator) applied to a plant. The elongation induction agent or the like may be provided in the form of a kit including, e.g., (i) the above gene or the above recombinant expression vector and (ii) any of various reagents for transforming a plant. Furthermore, the present invention also encompasses (i) a method for inducing root elongation of a plant by using the elongation induction agent or the like or (ii) a method for increasing biomass of a plant by using the elongation induction agent or the like. Such the method can be carried out by, e.g., scattering the elongation induction agent or the like, putting the elongation induction agent or the like into a plant, or using a transformation technique.

<6. Polynucleotide Having a Drought Stress-Specific Promoter Activity and Use Thereof>

Further, the inventors of the present invention analyzed a promoter region of the above-described CLCOL1 gene in the wild watermelon, so as to find the following fact: (i) The promoter region regulates expression of a specific gene in response to a change of an environment of a plant. (ii) Particularly, the promoter region is a promoter specifically inducing and regulating expression of a gene in response to a drought stress put on the plant. Furthermore, the inventors of the present invention found that the promoter region has a function of specifically expressing a gene in a root of the plant. Namely, the present invention encompasses a polynucleotide selected from the group consisting of the following (j) through (l): (j) a polynucleotide having the nucleotide sequence of SEQ ID NO: 3; (k) a polynucleotide having a nucleotide sequence with deletion, substitution, or addition of one or several nucleotides in the nucleotide sequence of SEQ ID NO: 3, the polynucleotide having a function as a promoter of regulating expression of a target gene in response to drought stress on a plant; and (l) a polynucleotide that hybridizes under stringent conditions with a polynucleotide having a nucleotide sequence which is complementary to a nucleotide sequence of the polynucleotide (j) or (k), the polynucleotide having a function as a promoter of regulating expression of a target gene in response to drought stress on a plant.

By inserting the above polynucleotide into a translation initiation site on a 5' terminal side of a gene encoding a target protein (hereinafter, such the gene is referred to as a "target gene"), it is possible to induce expression of the target gene in response to the drought stress on the plant and/or to express the target gene in the root at a high rate.

The above polynucleotide also encompasses a polynucleotide having a nucleotide sequence with substitution, deletion, addition, or insertion of at least one nucleotide in the nucleotide sequence of SEQ ID NO: 3, the polynucleotide having a function as a promoter of regulating expression of a target gene in response to drought stress on a plant (hereinafter, such the function is also referred to as a "dry-specific promoter activity"). The number of nucleotides which may be substituted, deleted, added, or inserted is not particularly limited, but is preferably one through several. For example, 1 through 10 nucleotides, preferably 1 through 5 nucleotides may be deleted in the nucleotide sequence of SEQ ID NO: 3; 1 through 10 nucleotide, preferably 1 through 5 nucleotides may be added to the nucleotide sequence of SEQ ID NO: 3; or 1 through 10 nucleotides, preferably 1 through 5 nucleotides may be substituted with another nucleotides in the nucleotide sequence of SEQ ID NO: 3.

Further, the present invention also encompasses a polynucleotide having a part of the nucleotide sequence of SEQ ID NO: 3 and having the dry-specific promoter activity. A part of the polynucleotide having the nucleotide sequence of SEQ ID NO: 3 which part is essential for the promoter activity can be identified by the following manner: Plasmids obtained by fusing (i) various deletion variants of the polynucleotide, for example, DNA fragments of various lengths each obtained by deleting a nucleotide(s) from an upstream region on its 5' terminal side to (ii) reporter genes such as β-glucuronidase (GUS) gene are introduced into hosts, and then promoter activities are assayed. Such the method for identifying the activity part is well-known to the person skilled in the art.

Such the mutant polynucleotide only needs to have the dry-specific promoter activity, and a level of the activity is not particularly limited. Preferably, however, the mutant polynucleotide substantially retains the dry-specific promoter activity of the polynucleotide having the nucleotide sequence of SEQ ID NO: 3. The expression "substantially retains the dry-specific promoter activity of the polynucleotide having the nucleotide sequence of SEQ ID NO: 3" intends the following state: In a case where the promoter activity is actually used, the promoter activity is maintained in such a degree that the promoter activity can be used almost in the same way under the same conditions as the polynucleotide having the nucleotide sequence of SEQ ID NO: 3.

The "dry-specific promoter activity" herein intends an activity of preferentially expressing, in a case where drought stress is put on a plant, the target gene at a higher level in at least part (preferably, a root) of a tissue or an organ of the plant body, as compared with a case where a plant of the same type is in a non-dry state. It is possible to evaluate the "dry-specific promoter activity" in a drought stress experiment conducted in the later-described Examples.

Mutagenesis for obtaining a mutant polynucleotide as those described above can be carried out by, e.g., the Kunkel method or the Gapped duplex method described in <1> above or any method corresponding thereto.

Furthermore, with use of a polynucleotide having the whole of or a part of the nucleotide sequence of SEQ ID NO: 3, the person skilled in the art would easily obtain, from various organisms, a new polynucleotide having another nucleotide sequence having the same function as that of the polynucleotide having the nucleotide sequence of SEQ ID NO: 3, i.e., the dry-specific promoter activity, and use the new polynucleotide. Such the polynucleotide having another nucleotide sequence can be obtained by, for example, (i)

hybridization with, under stringent conditions, a polynucleotide having a nucleotide sequence complementary to the nucleotide sequence of the polynucleotide having the whole of or a part of the nucleotide sequence of SEQ ID NO: 3 or (ii) PCR using a part of the nucleotide sequence as a primer. For procedures of the hybridization and PCR, the explanations made above are quoted as references. Examples of such the polynucleotide encompass polynucleotides having a high homology, namely, a polynucleotide having a nucleotide sequence having 80% or more, preferably 85% or more, more preferably 90% or more, further preferably 95% homology to the nucleotide sequence of SEQ ID NO: 3.

Note that the promoter activity of the obtained promoter region can be assayed by (i) incorporating the obtained promoter region into an upstream region of a gene whose expression level can be quantified and (ii) quantifying an expression level of the gene. Namely, it is possible to assay the promoter activity in a part of the obtained promoter region by (i) constructing a recombinant vector including the obtained promoter region and a predetermined gene and (ii) quantifying an expression level of the gene in a cell which has been transformed by use of the recombinant vector. Dry stress conditions therefor can be appropriately set by the person skilled in the art in reference to the later-described Examples.

Further, the present invention also encompasses a recombinant expression vector including the above polynucleotide as a promoter region. It is possible to construct such the recombinant expression vector by introducing, into a suitable vector, a cassette including the above polynucleotide having a downstream region to which the target gene is linked. For the recombinant expression vector, the explanations made in <2> above are quoted as references.

The target gene may be either one of an endogenous gene and a foreign gene each existing in a plant which is a target. For example, the gene may be, but is not limited to, a useful substance (e.g., a medicine, a pigment, or an aroma component) producing gene, a plant growth regulating (promoting/inhibiting) gene, a glucose metabolism-related gene, a disease and insect damage resistant (e.g., insect and vermin damage resistant, mold (fungus)/bacterium resistant, virus (disease) resistant) gene, or an environmental stress (low temperature, high temperature, dry, light disorder, ultraviolet) resistance-related gene.

Furthermore, the present invention also encompasses a transformant into which the above polynucleotide or the recombinant expression vector including that polynucleotide is introduced. It is possible to produce such the transformant by, e.g., transforming a target organism with use of the recombinant expression vector. The target organism is not limited to any particular kind. However, the target organism is preferably a plant.

The method for producing the transformant can be carried out by using any of various methods which have been already reported and established as appropriate. For specific explanations of this method, the descriptions in <3> and <4> above are quoted as references.

As described above, the gene of the present invention has the activity of inducing root elongation. Thus, highly expressing the gene of the present invention in a plant cell makes it possible to accelerate a speed of the root elongation without giving any effect in tissues other than the root. Therefore, the present invention can be used not only for the purpose of improving a resistance of a plant under adverse environmental stress such as drought stress but also for the purpose of increasing productivity of a plant by efficient absorption of nutrients or the purpose of increasing productivity of, e.g., a medicine or a herbal medicine by applying the present invention to plant tissue culture.

Specifically, the gene of the present invention and the techniques of use thereof provide the following excellent effects:

(I) Giving drought resistance to a plant: A plant in which the gene of the present invention is expressed and whereby growth of its root is increased exhibits an excellent ability to absorb water. Thus, such the plant can grow even under dry conditions.

(II) Leading to vigorous growth of a plant: A plant in which the gene of the present invention is expressed and whereby growth of its root is increased has an improved ability to absorb a nutrient and/or water. Thus, such the plant can be expected to grow vigorously.

(III) Improving stability: A plant in which the gene of the present invention is expressed and whereby growth of its root is increased can support its plant body firmly and stably by fixing the plant body onto a base (into the ground). Thus, it is easy to cultivate and maintain such the plant. This is very useful from a view point of agricultural value.

(IV) Producing a useful substance: There has been known a plant which produces and stores a useful substance such as alkaloid in its root. By expressing the gene of the present invention in such the plant so as to promote growth of a root of the plant, it is possible to efficiently produce a useful substance such as a medicine or a functional molecule. Further, by expressing the gene of the present invention in a cultured root instead of the plant individual, it is possible to produce the useful substance more easily and more efficiently.

The present invention is not limited to the description of the arrangements above, but may be altered by a skilled person within the scope of the specification. An embodiment based on a proper combination of technical means disclosed in different embodiments is encompassed in the technical scope of the present invention. All the references cited in the specification are quoted as references. The present invention will be described in more details based on the Examples. However, the present invention is not limited to the Examples.

EXAMPLES (1) Development of Drought Stress-Responsive Root System in Wild Watermelon Wild watermelons (*Citrullus lanatus* sp. No. 101117-1) of two weeks after germination were grown under dry conditions in which water irrigation was stopped. As a control group, wild watermelons of two weeks after germination were grown under wet conditions. Growing conditions therefor were as follows: light intensity of 250 µmol photons $m^{-2}s^{-1}$, 16 hours of light period/8 hours of dark period, temperature of 35/25° C., humidity of 50/60%, and ISO-LITE as soil.

The results are shown in (a) and (b) of FIG. 1. (a) of FIG. 1 shows how a water content in the soil changes, and (b) of FIG. 1 shows roots of the wild watermelons grown for 0 through 4 days under the dry conditions or the wet conditions. As shown in (b) of FIG. 1, outstanding development was observed in the root systems of the wild watermelons grown under the dry conditions, as compared with the control group grown under the wet conditions.

(2) Change in Dry Weight of Root of Watermelon Under Drought Stress

Figure 2:
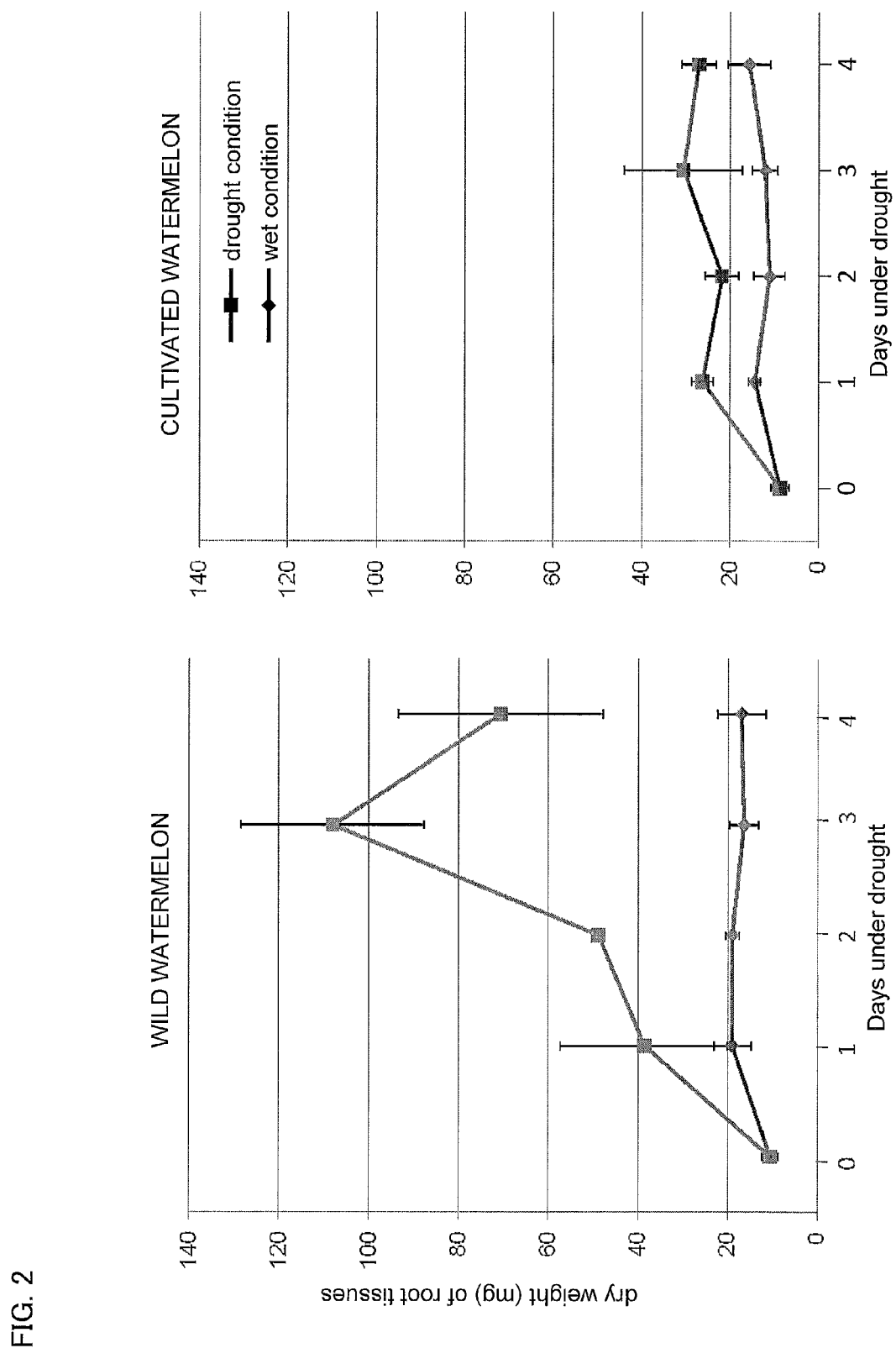
FIG. 2 shows a time-dependent change in dry weights of roots of a wild watermelon and a cultivated watermelon each of which was grown under the dry conditions.

Next, a time-dependent change in dry weights of roots of a wild watermelon and a cultivated watermelon each of which was grown under the dry conditions was studied. Note that the cultivated watermelon is known to have drought resistance which is weaker than that of the wild watermelon. The results are shown in FIG. 2. In FIG. 2, a graph on the left shows the dry weight of the root of the wild watermelon, whereas a graph on the right shows the dry weight of the root of the cultivated watermelon. As shown in FIG. 2, the dry weight of the root of the wild watermelon outstandingly increased under the dry conditions in which water irrigation was stopped. Further, after three days, the dry weight of the root of the wild watermelon grown under the dry conditions was approximately five times greater than that of the wild watermelon grown under grown under the wet conditions. From these results, the wild watermelon was assumed to have a characteristic root system developing mechanism which is dry responsive.

(3) Analysis of Time-Dependent Expression of CLCOL1 Gene in Root of Wild Watermelon Under Drought Stress Time-dependent expression of CLCOL1 gene in roots of the wild watermelons and the cultivated watermelons under drought stress was analyzed by quantitative RT-PCR. Specific procedures for the experiment are as follows.

Wild watermelons (sp. no. 101117-1) and cultivated watermelons (cv. Sanki) were grown for two weeks after germination in 500 ml of ISOLITE CG-1 (Isolite Insulating Products Co., Ltd.) in a climate chamber with 16 hours of light period/8 hours of dark period, temperature of 35/25° C., humidity of 50/60%, and light intensity of 250 μmol photons $m^{-2}s^{-1}$. One hour after the start of the light period everyday during this period, water containing 1000-fold dilution of Hyponex was given to the soil until a water content in the soil became 62%. After that, the wild watermelons and the cultivated watermelons were put into the dry conditions by stopping water irrigation. As a result, the water content in the soil dropped at a rate of approximately 9%/day. Here, the time point that the water irrigation was stopped was set as day 0. Four hours after the start of the light period during a period from day 0 to day 4, roots of plant bodies of three individuals were collected from the soil for time-course study. On the other hand, as a control under the wet conditions, plants of two weeks after germination were prepared in the same number. These control plants were continuously watered, and roots thereof were collected at the same timings as those for the plants grown in the state where the water irrigation was stopped. From the roots thus collected, total RNA was extracted by use of Plant RNA Isolation kit (Agilent). Further, cDNA was synthesized with use of reverse transcriptase ReverTra Ace-α-(Toyobo). The cDNA thus synthesized was subjected to the quantitative RT-PCR. The quantitative RT-PCR was carried out with use of SYBR Premix Ex Taq II (Takara) and Light Cycler 480 (Roche) under the following conditions:

Denature: 5 m 95° C., ramp rate 4.4° C./s. PCR: 45 cycles, 10 s 95° C., 10 s 60° C., 10 s 72° C., ramp rates 4.4° C./s, 2.2° C./s, 4.4° C./s (in each). Melting: 5 s 95° C., 15 s 65° C., ramping to 98° C., ramp rates 4.4° C./s, 2.2° C./s, 0.11° C./s (in each). Cooling: 10 s 50° C., ramping rate 1.1° C./s.

For correction, an endogenous actin gene was used. Primers used for detection of CLCOL1 and actin genes are as follows.

```
CLCOL1:
                                        (SEQ ID NO: 8)
  Forward: TTGAGGTTGGAGTTGTGCCG (SEQ ID NO: 9)
  Reverse: TACCTCAACACTCTCGCCTC Actin:
                                        (SEQ ID NO: 10)
  Forward: CATTCTCCGTTTGGACCTTGCT (SEQ ID NO: 11)
  Reverse: TCGTAGTTTTCTCAATGGAGGAACTG
```

Figure 3:
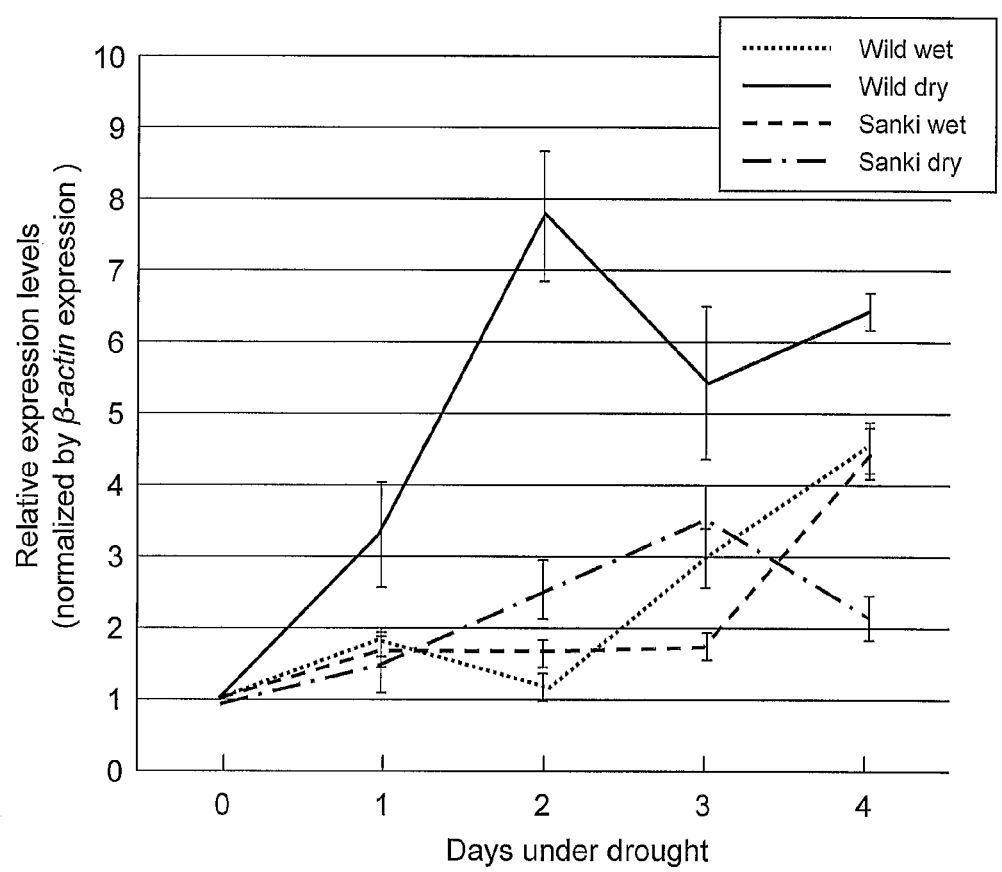
FIG. 3 shows a result of analysis of time-dependent expression of CLCOL1 gene in roots of wild watermelons under drought stress, the analysis having been carried out by quantitative RT-PCR.

The result is shown in FIG. 3. In FIG. 3, "Wild" represents the wild watermelon, whereas "Sanki" represents the cultivated watermelon. As shown in FIG. 3, expression of CLCOL1 gene increased in the root of the wild watermelon quickly after the start of application of the drought stress, and reached a peak at day 2 prior to a peak of development of the root system (day 3). The reason for this is considered as follows: After the gene is translated into a protein, expression of the gene appears as a phenotype of the development of the root system. Thus, expression of the gene reached the peak one day ahead of the peak of development of the root system.

(4) Expression Induction of CLCOL1 Gene in Hairy Root of Wild Watermelon with Use of Induction Vector Expression induction of CLCOL1 gene was carried out in a hairy root of the wild watermelon with use of a vector (XVE induction system) for expression induction by β-estradiol. Specific procedures for the experiment are as follows.

As the expression induction vector, pER8 vector (Zuo et al., Plant J. 24, 265-273, 2000) was used. ORF of CLCOL1 gene was inserted into a XhoI/SpeI restriction enzyme site in a downstream region of an inductive promoter ($O_{LexA}$-46) in pER8 vector, and the resultant was amplified by PCR so as to be cloned. Thus, pXVE-CLCOL1 was prepared. Primers used for the cloning are indicated below. The XhoI and SpeI site in each primer sequence corresponds to (i) a region from 4 to 9 bases from the 5' terminal in "Forward" and (ii) a region from 5 to 10 bases from the 5' terminal in "Reverse".

```
                                        (SEQ ID NO: 12)
  Forward: CCGCTCGAGGAATGGCTTCCAAGCTTTG (SEQ ID NO: 13)
  Reverse: GCCGACTAGTTTAGAAGGACGGAACGACG
``` pXVE-CLCOL1 was transformed into *Agrobacterium* (*Agrobacterium rhizogenes* ATCC 15834), and the transformant was used in hairy root induction using a hypocotyl of the wild watermelon. The hairy root induction of the wild watermelon was carried out according to the already-published method (Kajikawa et al., Plant Cell Rep. 29, 771-778, 2010). As a selection reagent, hygromycin having a final concentration of 2.5 mg/L was used.

Figure 4:
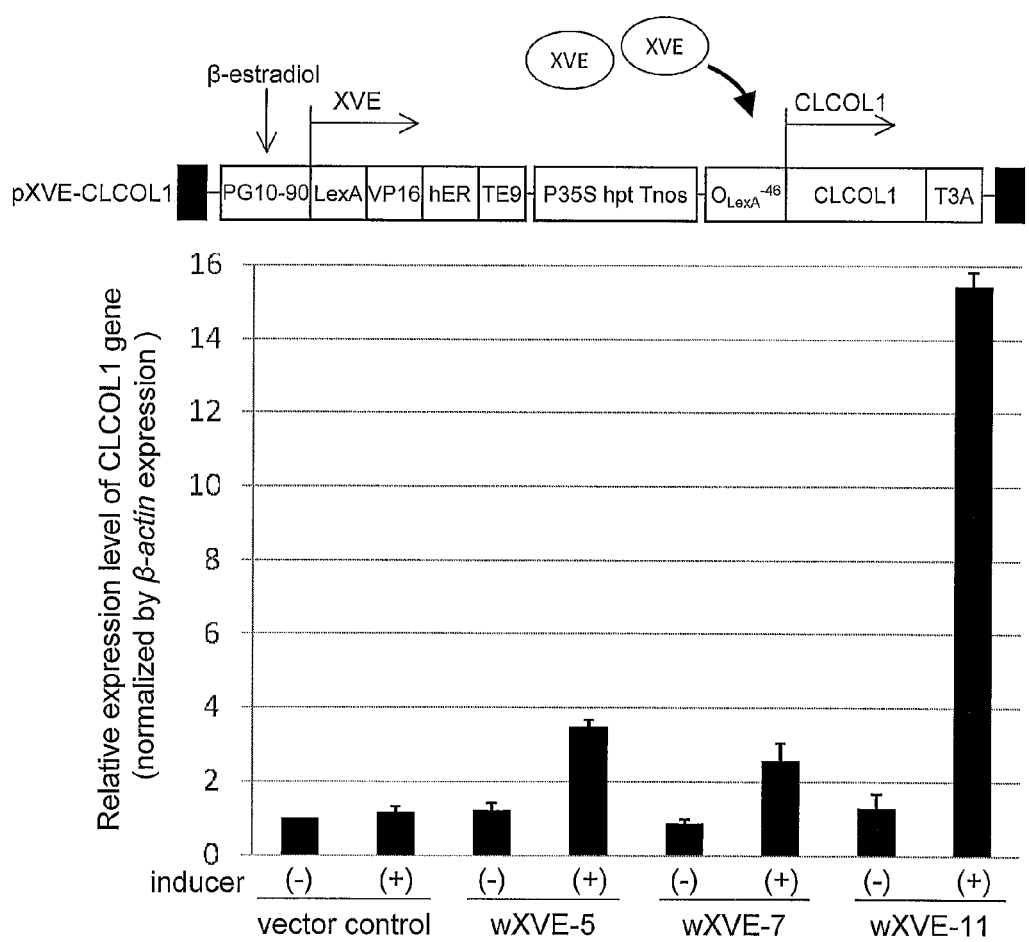
FIG. 4 shows a result of expression induction of CLCOL1 gene in hairy roots of wild watermelons, the expression induction having been carried out with use of an induction vector.

Three expression induction lines (wXVE-5, wXVE-7, and wXVE-11) were produced. To each of these three lines and a control line into which only pER8 vector was introduced, β-estradiol having a final concentration of 2 μM was added for expression induction of CLCOL1 gene. The result is shown in FIG. 4. In FIG. 4, the upper part shows a schematic view of the vector (pXVE-CLCOL1) prepared by incorporating CLCOL1 gene into the XVE induction vector, whereas the lower part shows a relative expression level of the gene. Approximately 5 cm-hairy roots of the three expression induction lines and the control line were each transplanted into a 2-µM estradiol containing medium and cultured therein for two days, and were subjected to analysis of the expression level of the gene. As a control, hairy roots of the three expression induction lines and the control line were each cultured in a medium not containing estradiol, and were subjected to analysis of expression of the gene similarly. The expression level of CLCOL1 gene was analyzed by the quantitative RT-PCR as described in the section (3) above. As shown in FIG. 4, it was confirmed that expression of CLCOL1 gene was induced by addition of β-estradiol in each of the three expression induction lines.

Next, how the increase in the expression level of CLCOL1 gene affects growth of a hairy root was studied. Specific procedures for the experiment are as follows: Approximately 5 cm-hairy roots of the three expression induction lines and the control line were each transplanted into a 2-µM estradiol containing medium. From the tip of each of the hairy roots at that time, how long the hairy root elongated was measured for four days.

Figure 5:
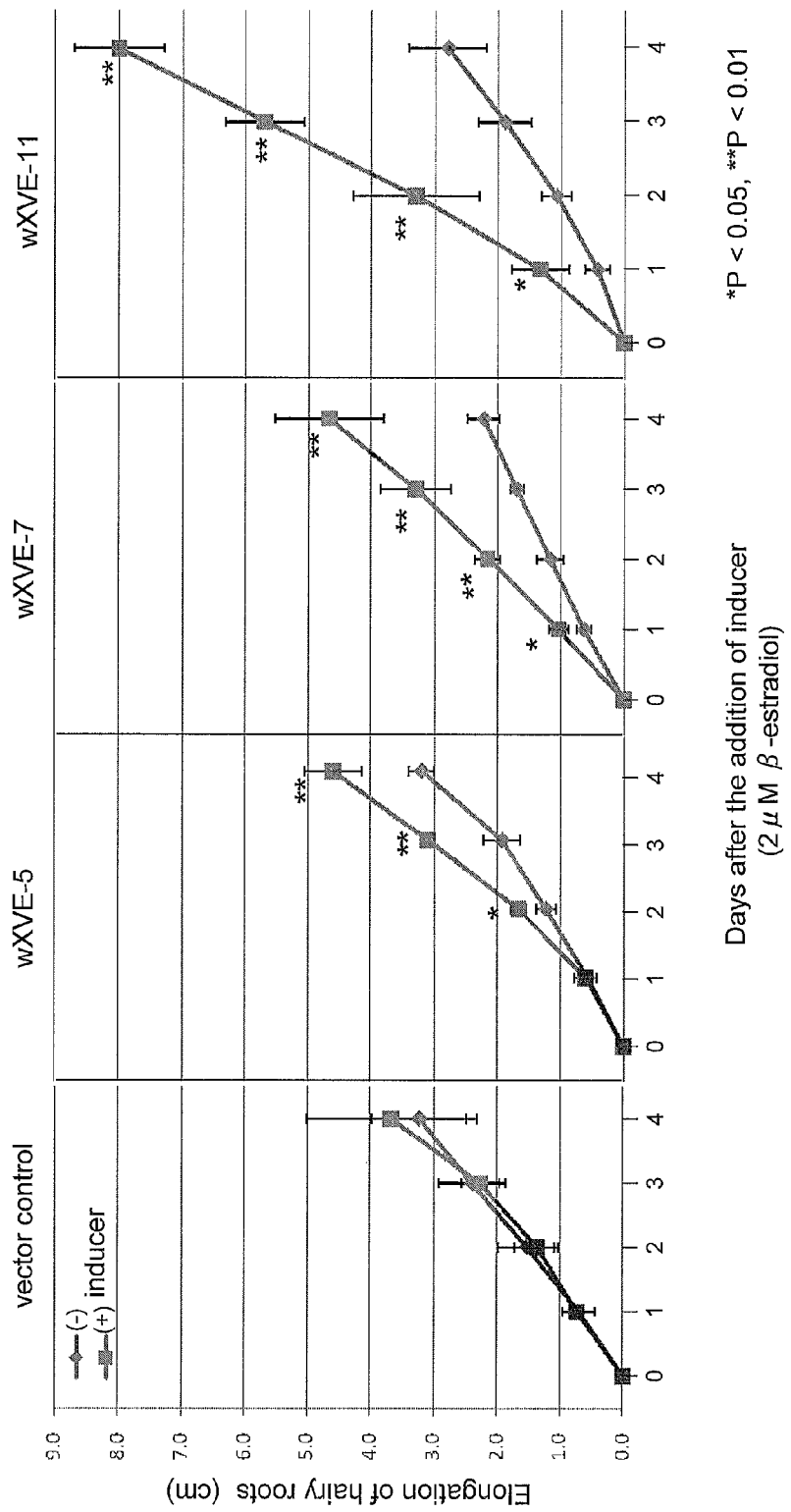
FIG. 5 shows how an increase in an expression level of CLCOL1 gene affects growth of a hairy root.

The result is shown in FIG. 5. As shown in FIG. 5, in each of the lines into which pXVE-CLCOL1 vector was introduced, elongation of the hairy root was notably promoted by increasing the expression level of CLCOL1 gene by addition of β-estradiol. This strongly suggests that CLCOL1 gene relates to regulation of molecules for development of the root system of the wild watermelon under the dry conditions.

(5) How Expression of CLCOL1 Gene in Arabidopsis thaliana Affects Growth of Root Two lines of *Arabidopsis thaliana* transformants in which CLCOL1 gene was highly expressed were prepared (CLCOL1ox-3 and CLCOL1ox-17). Specific procedures for the experiment are as follows.

CLCOL1 gene expression vector was prepared with use of pGWB2 vector (Nakagawa et al., J. Biosci. Bioeng. 104, 34-41, 2007) by Gateway cloning (Invitrogen). CLOCL1 gene was cloned into pDONR221 (Invitrogen) by BP reaction. Primers used therefor are as follows:

```
                                      (SEQ ID NO: 14)
Forward: AAAAAGCAGGCTCCGGAATGGCTTCCAAGCTTTG (SEQ ID NO: 15)
Reverse: AGAAAGCTGGGTTAGAAGGACGGAACGACG
```

Further, the resultant was cloned into pGWB2 by LR reaction, so as to prepare a CLCOL gene expression vector, pGWB2-CLCOL1. pGWB2-CLCOL1 was transformed into *Agrobacterium* (*Agrobacterium tumefaciens* MP90), and *Arabidopsis thaliana* was infected therewith by the floral dip method. T1 transformants thus obtained were subjected to selection by hygromycin having a final concentration of 25 mg/L, so that T2 seeds, which are progeny obtained from self-pollination of T1 transformants thus selected. The T2 seeds were subjected to selection with hygromycin. Then, two lines (CLCOL1ox-3 and CLCOL1ox-17) whose selection ratio of resistant to non-resistant was 3:1, i.e., which had one copy of expression cassette inserted, were selected. Further, homo-type T3 seeds of these two lines were obtained. The homo-type T3 seeds of CLCOL1ox-3 and CLCOL1ox-17 and wild seeds were sowed in a non-selection medium. Then, from the first day (day 1) after germination, how long their main roots elongated was measured for seven days.

Figure 6:
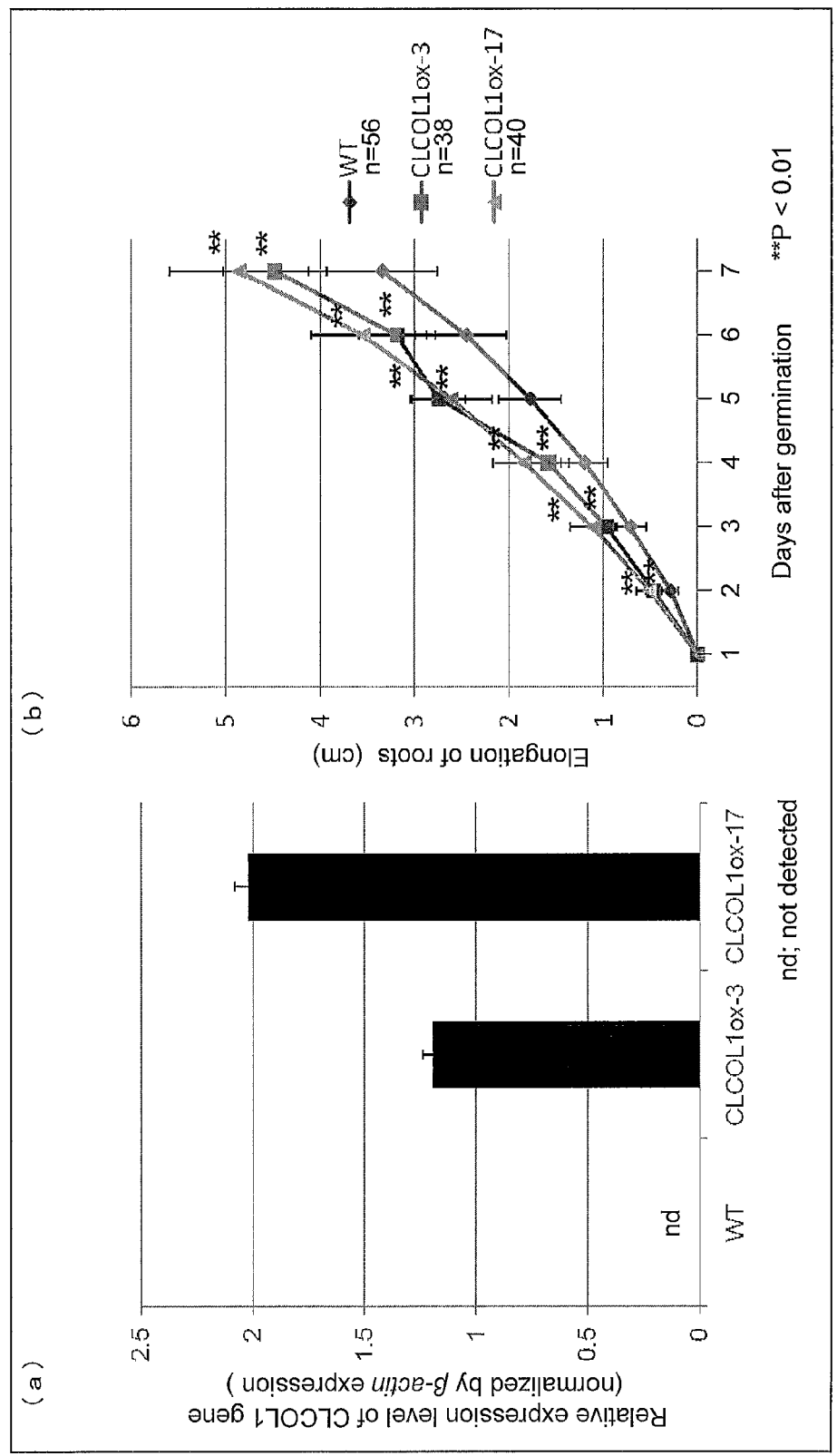
FIG. 6 shows a result of analysis on how a root system of *Arabidopsis thaliana* transformant in which CLCOL1 gene was highly expressed developed after germination.

On each of these two lines of *Arabidopsis thaliana* transformants, development of the root system after germination was analyzed. The result is shown in FIG. 6. As shown in FIG. 6, in each of the *Arabidopsis thaliana* transformants in which CLCOL1 gene was highly expressed, elongation of the main root after germination was notably promoted as compared with the wild type (WT). This result shows that CLCOL1 gene has a function of promoting development of the root system even in a plant body of other kind.

(6) How Expression of CLCOL1 Gene in Rice Affects Growth

A rice in which CLCOL1 gene was highly expressed (cultivar: yukihikari) was produced.

CLCOL1 gene was recombined into GATEWAY entry vector (pDONR221: kanamycin resistant vector). The resultant was transformed into DH5α competent cell, and the transformant was then subjected to plasmid extraction for sequencing. Then, a plasmid having an insert which was the same as the sequence information was obtained. LR reaction was carried out between pDONR221 entry vector having the "attL1-CLCOL1 (1014 bp)-attL2" and pDEST1 destination vector having the "attR1-CmRccdB-attR2", so that an expression vector was prepared.

A solution made of 20 µl of a reaction solution containing approximately 600 ng of CLCOL1/pDONR221 and approximately 2 µg of pDEST1Red was adjusted to be 16 µl by TE. Finally, 4 µl of Gateway® LR Clonase II Enzyme Mix (Invitrogen) was added thereto, and was left at 25° C. overnight for reaction. To the resultant, 2 µl of Proteinase K was added, and was incubated at 37° C. for 10 minutes in order to stop the LR reaction. To the resultant, 30 µl of MilliQ was added for ethanol precipitation. The resultant was transformed into GeneHogs competent cell by the electroporation method. The transformant was applied onto an LB agar medium containing 50 µg/ml kanamycin and 35 µg/ml hygromycin, and was cultured at 37° C. overnight.

A resultant colony was cultured in 2 ml of TB medium containing 50 µg/ml kanamycin and 35 µg/ml hygromycin at 37° C. overnight. From the culture solution, a plasmid was extracted by the miniprep method, and Afl II & Pac I digestion pattern check was carried out. Further, the plasmid was sequenced from both ends with use of pDEST1-FW primer and pDEST1-RV primer by a fluorescence sequencer (ABI PRISM 3100 Genetic Analyzer, available from Applied Biosystems). Primers used therefor are as follows:

```
                                      (SEQ ID NO: 16)
Forward: TTAGCCCTGCCTTCATACGCTATTT (SEQ ID NO: 17)
Reverse: TAAATAACGTCATGCATTACATGTT
```

1 µl of the plasmid thus sequenced was transformed into *Agrobacterium* (LBA4404) competent cell by the electroporation method. The resultant was suspended in 1 ml of SOC medium, and was then cultured at 28° C. for 1 through 2 hours. Then, the resultant was applied onto an LB agar medium containing 50 µg/ml kanamycin and 35 µg/ml hygromycin, and was cultured at 28° C. for one through two nights.

A resultant colony of CLCOL1/pDEST1/LBA4404 was cultured in 2 ml of TB medium containing 50 µg/ml kanamycin and 35 µg/ml hygromycin at 28° C. for two nights. From the culture solution, a plasmid was extracted and sequenced. A colony of *Agrobacterium* having a plasmid whose sequence had been confirmed was streaked onto an AB agar medium containing 50 µg/ml kanamycin and 35 µg/ml hygromycin. The transformation was carried out by a method of infecting an immature embryo with *Agrobacterium*.

Individuals redifferentiated from a callus derived from the immature embryo were subjected to selection with 50 mg/l hygromycin, so that transformants were selected. T0 individuals thus obtained were cultivated in a greenhouse, and seeds were collected therefrom.

56 seeds of each of (i) four lines of T1, from which the seeds were collected, and (ii) rice cultivar yukihikari, which was used as a control, were sowed. After 10 days, leaves were cut out therefrom, and were assayed with 100 mg/l hygromycin. From the T1 lines, hygromycin-resistant individuals were selected. 24 individuals of each line were individually planted in their respective vinyl plant pots each having a diameter of 10.5 cm and a height of 8 cm and containing compost for rice (for all the individuals of yukihikari serving as the control, hygromycin sensitivity was confirmed). The individuals were then cultivated for 136 days, and their growth was observed (see FIG. 7). Further, a culm length, a maximum ear length, and a total ear weight were measured for each of the individuals (see Table 2). After the cultivation was ended, each stock was pulled out from the pot, and root elongation thereof was observed (see FIG. 8).

TABLE 2

Averages of Measurements on Traits of Each Line

|  | Culm Length (cm) | Max. Ear Length (cm) | Total Ear Weight (g) |
| --- | --- | --- | --- |
| CLCOL1-1 | 73.6* | 18.4* | 4.7* |
| CLCOL1-2 | 74.2* | 19.4* | 4.2* |

TABLE 2-continued

Averages of Measurements on Traits of Each Line

|  | Culm Length (cm) | Max. Ear Length (cm) | Total Ear Weight (g) |
| --- | --- | --- | --- |
| CLCOL1-3 | 73.7* | 17.4 | 4.0 |
| CLCOL1-4 | 64.7 | 18.7* | 3.2 |
| Control | 65.2 | 17.0 | 3.1 |

*A value for which a significant difference from the control was found by t-test.

Figure 7:
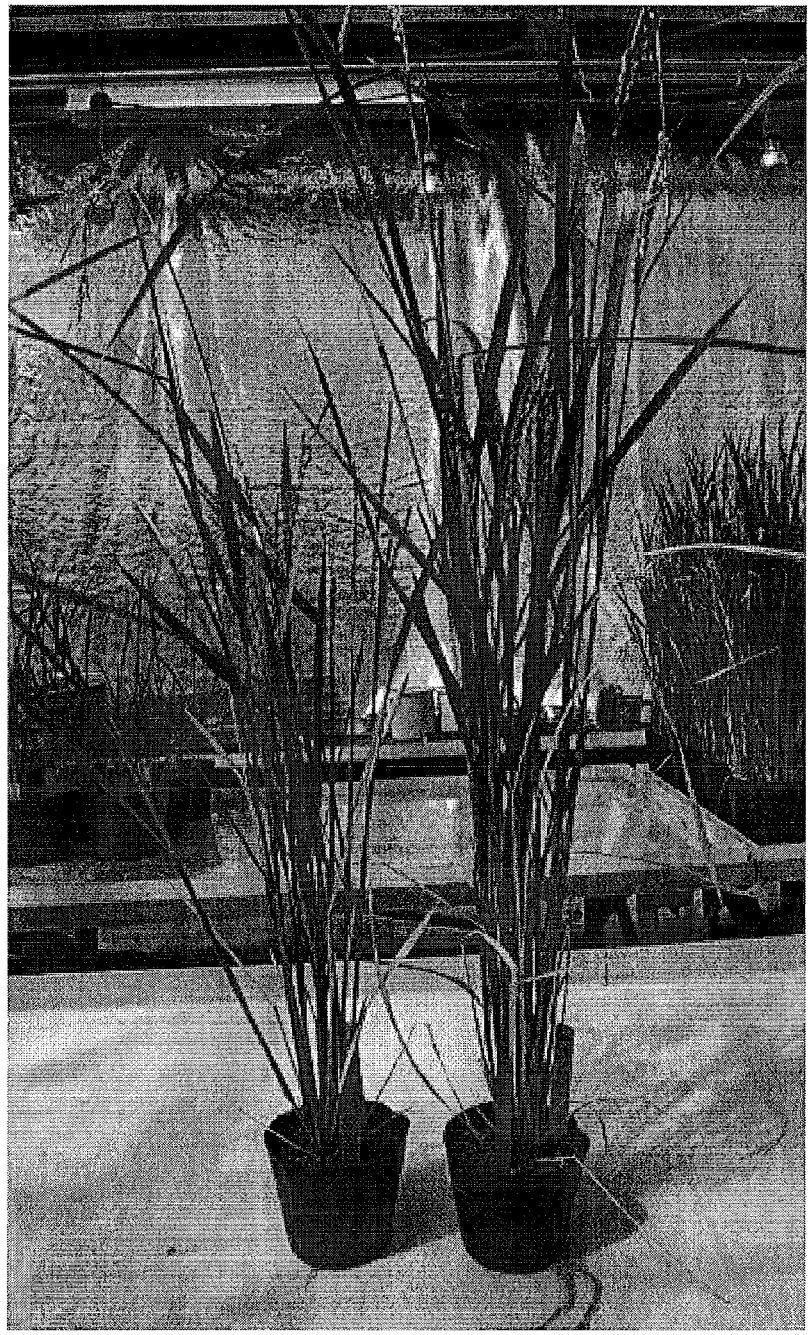
FIG. 7 shows a result of observation on growth of (i) a plant transformed by CLCOL1 gene and (ii) a control plant.
Figure 8:
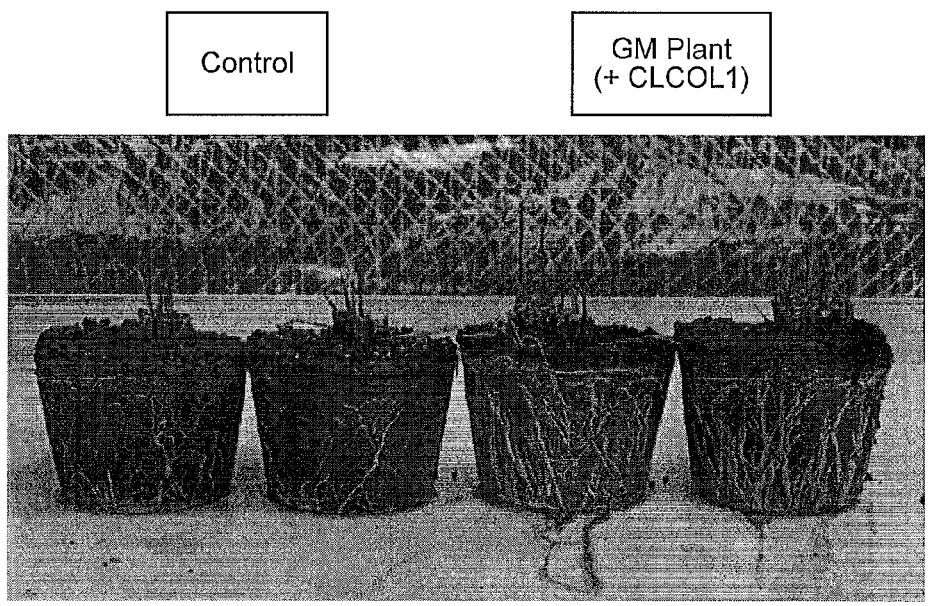
FIG. 8 shows a result of observation on how roots of plants transformed by CLCOL1 gene and a control plant elongated, the observation having been carried out after these plants were pulled out from their pots.

As shown in FIG. 7, the rice into which CLCOL1 gene was introduced had an above-ground part grown clearly better than that of the control, the non-transformant rice. Further, as shown in FIG. 8, the rice into which CLCOL1 gene was introduced had a root grown clearly better than that of the control, the non-transformant rice.

As shown in Table 2, among the measured traits, as to the culm length, three lines of the four lines into which CLCOL1 was introduced exhibited a higher value than that of the control, yukihikari; as to the maximum ear length, three lines of the four lines exhibited a higher value than that of the control, yukihikari: and as to the total ear weight, two lines of the four lines exhibited a higher value than that of the control, yukihikari.

Further, the following growing characteristic was confirmed: In the individual into which CLCOL1 is introduced, ear emergence tends to be delayed for 1 through 4 weeks.

INDUSTRIAL APPLICABILITY

The present invention is applicable to various industries such as food production, greening of a desert, breeding of plants, development of fuels utilizing biomass, and production of useful substances (e.g., medicines and functional molecules) with use of cultured plant cells.

The invention claimed is:

1. A plant in which root elongation is induced or whose biomass is increased, said plant being transformed by a gene selected from the group consisting of the following (a) through (c):
   (a) a gene encoding a protein having the amino acid sequence of SEQ ID NO: 1;
   (b) a gene encoding a protein having an amino acid sequence having at least 95% identity to the amino acid sequence of SEQ ID NO: 1, wherein the protein induces root elongation of a plant or increases biomass of a plant; and
   (c) a gene having the nucleotide sequence of SEQ ID NO: 2.

2. A plant which is a progeny, an offspring, or a clone of the plant recited in claim 1.

3. A breeding material of the plant recited in claim 1, wherein said breeding material contains the gene.

4. A breeding material of the plant recited in claim 2, wherein said breeding material contains the gene.

5. The plant according to claim 1, said plant being transformed by a gene encoding a protein having an amino acid sequence having at least 96% homology to the amino acid sequence of SEQ ID NO: 1, wherein the protein induces root elongation of a plant or increases biomass of a plant.

6. The plant according to claim 1, said plant being transformed by a gene encoding a protein having an amino acid sequence having at least 97% homology to the amino acid sequence of SEQ ID NO: 1, wherein the protein induces root elongation of a plant or increases biomass of a plant.

7. The plant according to claim 1, said plant being transformed by a gene encoding a protein having an amino acid sequence having at least 99% homology to the amino acid sequence of SEQ ID NO: 1, wherein the protein induces root elongation of a plant or increases biomass of a plant.

* * * * *

SEQUENCE LISTING

```
<160> NUMBER OF SEQ ID NOS: 17

<210> SEQ ID NO 1
<211> LENGTH: 337
<212> TYPE: PRT
<213> ORGANISM: Citrullus lanatus

<400> SEQUENCE: 1

Met Ala Ser Lys Leu Cys Asp Ser Cys Lys Ser Ala Thr Ala Thr Leu
1               5                   10                  15

Phe Cys Arg Ala Asp Ser Ala Phe Leu Cys Leu Gly Cys Asp Ser Lys
            20                  25                  30

Val His Ala Ala Asn Lys Leu Ala Ser Arg His Ala Arg Val Trp Val
        35                  40                  45

Cys Glu Val Cys Glu Gln Ala Pro Ala His Val Thr Cys Lys Ala Asp
    50                  55                  60

Ala Ala Ala Leu Cys Leu Thr Cys Asp His Asp Ile His Ser Gly Asn
65                  70                  75                  80

Pro Leu Ala Arg Arg His Glu Arg Val Pro Val Thr Pro Phe Tyr Asp
```

```
                        85                  90                  95
Thr Ser Asn Ser Asp Asn Ser Leu Ala Val Lys Pro Ser Ala Ala Ile
                    100                 105                 110
Asn Phe Leu Asp Asp Arg Tyr Phe Ser Asp Val Asp Gly Asp Ala Ala
                115                 120                 125
Asp Val Ser Arg Glu Glu Ala Glu Ala Ala Ser Trp Leu Leu Pro Asn
            130                 135                 140
Pro Asn Pro Lys Ala Ile Glu Ser Ser Asp Leu Asn Ser Gly Lys Phe
145                 150                 155                 160
Glu Phe Pro Glu Met Asp Pro Tyr Leu Asp Leu Asp Tyr Gly His Val
                165                 170                 175
Asp Pro Lys Leu Glu Ala Gln Glu Gln Asn Ser Ser Gly Ala Asp Gly
                180                 185                 190
Val Val Pro Val Gln Ser Lys Gly Val Asn Leu Ser Ser Val Asn Asp
                195                 200                 205
Arg Cys Phe Gly Ile Asp Phe Pro Ser Thr Lys Ser Phe Pro Tyr Gly
            210                 215                 220
Tyr Asn Pro Gln Ser Ile Ser His Ser Val Ser Ser Ser Ile Glu
225                 230                 235                 240
Val Gly Val Val Pro Asp Gly Asn Ala Met Thr Asp Val Ser Asn Pro
                245                 250                 255
Tyr Thr Lys Pro Ser Thr Glu Ser Thr Val Gln Pro Leu Gln Ile Ser
                260                 265                 270
Pro Ala Asp Arg Glu Ala Arg Val Leu Arg Tyr Arg Glu Lys Arg Lys
                275                 280                 285
Asn Arg Lys Phe Glu Lys Thr Ile Arg Tyr Ala Ser Arg Lys Ala Tyr
            290                 295                 300
Ala Glu Thr Arg Pro Arg Ile Lys Gly Arg Phe Ala Lys Arg Thr Asp
305                 310                 315                 320
Ile Glu Leu Asp Val Asp Arg Val Ser Gly Tyr Gly Val Val Pro Ser
                325                 330                 335
Phe

<210> SEQ ID NO 2
<211> LENGTH: 1014
<212> TYPE: DNA
<213> ORGANISM: Citrullus lanatus

<400> SEQUENCE: 2
atggcttcca agctttgtga ctcctgtaag tcggccaccg ccactctctt ctgccgagct    60
gactctgcct tcctttgcct tggctgtgac tccaaagttc acgccgccaa caaactcgcc   120
tctcgccatg ctcgcgtttg ggtctgtgaa gtttgcgagc aagctcctgc tcatgtaacc   180
tgcaaggctg acgccgccgc tctctgcctc acttgcgacc acgatattca ctctgctaat   240
cccctcgctc gccgtcacga gcgagttccc gtcacgcctt tctacgacac tccaactcc    300 gacaactcac tcgccgttaa acctagcgct gcaatcaact tcctcgatga ccgttacttc   360
tccgatgtcg acggtgatgc cgctgatgtt agtagagaag aagccgaggc tgcttcctgg   420
cttcttccga accctaaccc taaggcaatc gaaagttcag atctgaactc agggaagttt   480
gagtttccag aaatggatcc ttacctagat ctggattacg gccatgtaga tccgaaattg   540
gaagcgcaag agcaaaacag ctccggcgcc gatggagttg ttccggttca gagcaaaggc   600
gttaatctct catctgtaaa cgatcgctgc ttcggcatag atttccccag caccaaatcg   660
```

```
ttcccgtacg gttacaatcc tcagtcaatc agtcacagtg tatcatcctc ttcgattgag    720
gttggagttg tgccggatgg gaacgcgatg acggatgtat caaatccgta cactaaaccg    780
tcgacggaat cgacggttca accgctgcaa atctcgccgg cggatcggga ggcgagagtg    840
ttgaggtaca gagagaagag gaagaacaga aaattcgaaa agacgatccg atacgcatct    900
cgtaaggctt acgccgagac gagacctcga atcaaaggac ggttcgccaa acggacggac    960
atcgaacttg atgttgacag agtgagtgga tacggcgtcg ttccgtcctt ctaa         1014
```

<210> SEQ ID NO 3
<211> LENGTH: 1945
<212> TYPE: DNA
<213> ORGANISM: Citrullus lanatus

<400> SEQUENCE: 3

```
gtcgagtgag gatgaacaga accgacaatt gggccgcttt cctgggccga cagaactaga     60
agtctctgga aaaataaggt caccccatgc ttttattaga cacacctttta aagcctttc    120 ccctccctac taagttataa aacaatctct ttttttctta ttgaactcta atatgtttca    180
aagatgaatg gctcaatcaa ctctctttca gtttgataat ttatcacatc gttaaagtta    240
tatataattt tattcaaaga gttaagtgag tgtttgggaa gagtcattgt tatttggtcc    300
tatgaatttt tgaatctatt atgggcccca caacgtatta acatcaattt catggcttat    360
taacctttac attgtaataa ggtagtaact acacttctaa ttcctcctct tcttcttagt    420
atttggacag aggctttctt tgattggctt ttcctccttg ttgggttgaa attttaataa    480
accccccatt ttaactaaaa acaaccgtta catagttaca ctgtgggctc cacaactaaa    540
caattttgca tcacttcaaa caccctttaa atgttcatca atggggtgta gtatatatat    600
attacattaa tgtgatataa taattttttc tccatactat ctcaattcat tatctgacat    660
gatataagaa ttctataaaa atgtggggct agtgaaataa tctctatatc acctaatgaa    720
agtcaaatga taaatagaag aagcacatac aattatagaa tagaaaattt tcaaacattt    780
tcaaactagg gtagtagtag aaactttctc ggtatattga gaaactataa tattgcaact    840
tttaaaagta atagttttaac caaaattacg ccgcttttaa cctagacaaa cgtaacaaat    900
caatgataat ttgaaaaatg agttccattt gattatatcg gttgttgttt acttatgttt    960
tgtaattgta atgaaatatg gggcccaatt ccaagtttgt aatcgaataa cgcaatccaa   1020
ttgaggcgtg aatggtgatc aatccaacta cattacaaaa ttacgtggga cccattagcc   1080
aatacgctac ggttatcttt attgttactg ttataacata agaattatga atctatcact   1140
aaactgtata cagattcata attctaagta aatttgataa aaacaattca attatatttg   1200
caattgtagc cgttatggat tggtaaacat agccttatat cattaaccaa aatatagaat   1260
ttcaaatctt aactctcaca cccaaataaa tgatacaata tgttagtaat taagaaattt   1320
gtggttagta aattaatcaa tttgagcctt atagtatgga aaaaaaatta gaatttactc   1380
caaatagttt ggaaagttag aatttggtct ttatagttgg gagaaaatta gaattttgtc   1440
cttatggttc gaaaaaaaag ttaaaattta gtcactaatt tgaggctatt taagaacatt   1500
ttatcaaaca aaaaaactaa attataattt taaatgatag taatcaaatc aaccaagaac   1560
actctaataa aaaaaggtaa gaaaagaaa tatggagtct cacatgaaat ccggaggcca   1620
gacaagaagt tcacatggac cccactctta acttttcctt tgcctcacct cgtgttgaac   1680
ttaaaaaaaa aaaagaaaaa aaactttctt tttcaacccc ctaaatattt attaattttc   1740
cccttcactg aaggcgataa atattttggg tttctatggc taagcctcgc ccacgtgttt   1800
```

```
atctttcatt cgtccatgac tggatttcgt tggctccacc ggatagactc gtacacgcct    1860
gattaactaa aacaatacta tagaaccaaa acagattgaa gagagacaca ttacatacca    1920
ttttcagttt tccgccattg gagca                                          1945
```

<210> SEQ ID NO 4
<211> LENGTH: 337
<212> TYPE: PRT
<213> ORGANISM: Citrullus lanatus

<400> SEQUENCE: 4

```
Met Ala Ser Lys Leu Cys Asp Ser Cys Lys Ser Ala Thr Ala Thr Leu
1               5                   10                  15

Phe Cys Arg Ala Asp Ser Ala Phe Leu Cys Leu Gly Cys Asp Ser Lys
            20                  25                  30

Val His Ala Ala Asn Lys Leu Ala Ser Arg His Ala Arg Val Trp Val
        35                  40                  45

Cys Glu Val Cys Glu Gln Ala Pro Ala His Val Thr Cys Lys Ala Asp
    50                  55                  60

Ala Ala Ala Leu Cys Leu Thr Cys Asp His Asp Ile His Ser Ala Asn
65                  70                  75                  80

Pro Leu Ala Arg Arg His Glu Arg Val Pro Val Thr Pro Phe Tyr Asp
                85                  90                  95

Thr Ser Asn Ser Asp Asn Ser Leu Ala Val Lys Pro Ser Ala Ala Ile
            100                 105                 110

Asn Phe Leu Asp Asp Arg Tyr Phe Ser Asp Val Asp Gly Asp Ala Ala
        115                 120                 125

Asp Val Ser Arg Glu Glu Ala Glu Ala Ala Ser Trp Leu Leu Pro Asn
    130                 135                 140

Pro Asn Pro Lys Ala Ile Glu Ser Ser Asp Leu Asn Ser Gly Lys Phe
145                 150                 155                 160

Glu Phe Pro Glu Met Asp Pro Tyr Leu Asp Leu Asp Tyr Gly His Val
                165                 170                 175

Asp Pro Lys Leu Glu Ala Gln Glu Gln Asn Ser Ser Gly Ala Asp Gly
            180                 185                 190

Val Val Pro Val Gln Ser Lys Gly Val Asn Leu Ser Glu Asn Asp
        195                 200                 205

Arg Cys Phe Gly Ile Asp Phe Pro Ser Thr Lys Ser Phe Pro Tyr Gly
    210                 215                 220

Tyr Asn Pro Gln Ser Ile Ser His Ser Val Ser Ser Ser Ile Glu
225                 230                 235                 240

Val Gly Val Val Pro Asp Gly Asn Ala Met Thr Asp Val Ser Asn Pro
                245                 250                 255

Tyr Thr Lys Pro Ser Thr Glu Ser Thr Val Gln Pro Leu Gln Ile Ser
            260                 265                 270

Pro Ala Asp Arg Glu Ala Arg Val Leu Arg Tyr Arg Glu Lys Arg Lys
        275                 280                 285

Asn Arg Lys Phe Glu Lys Thr Ile Arg Tyr Ala Ser Arg Lys Ala Tyr
    290                 295                 300

Ala Glu Thr Arg Pro Arg Ile Lys Gly Arg Phe Ala Lys Arg Thr Asp
305                 310                 315                 320

Ile Glu Leu Asp Val Asp Arg Val Ser Gly Tyr Gly Val Val Pro Ser
                325                 330                 335

Phe
```

<210> SEQ ID NO 5
<211> LENGTH: 1014
<212> TYPE: DNA
<213> ORGANISM: Citrullus lanatus

<400> SEQUENCE: 5

```
atggcttcca agctttgtga ctcctgtaag tcggccaccg ccactctctt ctgccgagct      60
gactctgcct tcctatgcct tggctgtgac tccaaagttc acgccgccaa caaactcgcc     120
tctcgccatg ctcgcgtttg ggtctgtgaa gtttgcgagc aagctcctgc tcatgtaacc     180
tgcaaggctg acgccgccgc tctctgcctc acttgcgacc acgatattca ctctgctaat     240
cccctcgctc gccgtcacga gcgagttccc gtcacgcctt tctacgacac ctccaactcc     300
gacaactcac tcgccgttaa acctagcgct gcaatcaact cctcgatgac cgttacttc     360
tccgacgtcg acggtgatgc cgctgatgtt agtagagaag aagccgaggc tgcttcctgg     420
cttcttccga accctaaccc taaggcaatc gaaagttcag atctgaactc agggaagttt     480
gagtttccag aaatggatcc ttacctagat ctggattacg ccatgtaga tccgaaattg     540
gaagcgcaag agcaaaacag ctccggcgcc gatggagttg ttccggttca gagcaaaggc     600
gttaatctct catccgtaaa cgatcgctgc ttcggcatag atttccccag caccaaatcg     660
ttcccgtacg gttacaatcc tcagtcaatc agtcacagtg tatcatcctc ttcgattgag     720
gttggagttg tgccggatgg gaacgcgatg acggatgtat caaatccgta cactaaaccg     780
tcgacggaat cgacggttca accgctgcaa atctcgccgg cggatcggga ggcgagagtg     840
ttgaggtaca gagagaagag gaagaacaga aaattcgaaa agacgatccg atacgcatct     900
cgtaaggctt acgccgagac gagacctcga atcaaaggac ggttcgccaa acggacggac     960
atcgaacttg atgttgacag agtgagtgga tacggcgtcg ttccgtcctt ctaa          1014
```

<210> SEQ ID NO 6
<211> LENGTH: 337
<212> TYPE: PRT
<213> ORGANISM: Cucumis sativus

<400> SEQUENCE: 6

Met Ala Ser Lys Leu Cys Asp Ser Cys Lys Ser Ala Thr Ala Thr Leu
1               5                   10                  15

Phe Cys Arg Ala Asp Ser Ala Phe Leu Cys Leu Gly Cys Asp Ser Lys
                20                  25                  30

Val His Ala Ala Asn Lys Leu Ala Ser Arg His Ala Arg Val Trp Val
            35                  40                  45

Cys Glu Val Cys Glu Gln Ala Pro Ala His Val Thr Cys Lys Ala Asp
        50                  55                  60

Ala Ala Ala Leu Cys Leu Thr Cys Asp His Asp Ile His Ser Ala Asn
65                  70                  75                  80

Pro Leu Ala Arg Arg His Glu Arg Val Pro Val Thr Pro Phe Tyr Asp
                85                  90                  95

Thr Ser Asn Ser Asp Asn Ser Leu Pro Val Lys Pro Ser Ala Ala Ile
                100                 105                 110

Asn Phe Leu Asp Asp Arg Tyr Phe Ser Asp Val Asp Ala Asp Ala Ala
            115                 120                 125

Asp Val Ser Arg Glu Glu Ala Glu Ala Ala Ser Trp Leu Leu Pro Asn
        130                 135                 140

Pro Asn Pro Lys Ala Ile Glu Ser Ser Asp Leu Asn Ser Gly Lys Phe

```
                145                 150                 155                 160
            Glu Phe Pro Glu Met Asp Pro Tyr Leu Asp Leu Asp Tyr Ser His Val
                            165                 170                 175

Asp Pro Lys Leu Glu Ala Gln Glu Gln Asn Ser Ser Gly Ala Asp Gly
                        180                 185                 190

Val Val Pro Val Gln Ser Lys Gly Val His Leu Ser Ser Ala Asn Asp
                    195                 200                 205

Arg Cys Leu Gly Ile Asp Phe Thr Gly Thr Lys Ser Phe Pro Tyr Gly
                210                 215                 220

His Asn Pro Gln Ser Ile Ser His Ser Val Ser Ser Ser Ile Glu
            225                 230                 235                 240

Val Gly Val Val Pro Asp Gly Asn Ala Met Thr Asp Val Ser Asn Pro
                            245                 250                 255

Tyr Thr Lys Pro Ser Thr Glu Ser Val Gln Pro Leu Gln Ile Ser
                        260                 265                 270

Pro Ala Asp Arg Glu Ala Arg Val Leu Arg Tyr Arg Glu Lys Arg Lys
                    275                 280                 285

Asn Arg Lys Phe Glu Lys Thr Ile Arg Tyr Ala Ser Arg Lys Ala Tyr
                290                 295                 300

Ala Glu Thr Arg Pro Arg Ile Lys Gly Arg Phe Ala Lys Arg Thr Asp
            305                 310                 315                 320

Ile Glu Leu Asp Val Asp Arg Val Ser Gly Tyr Gly Val Val Pro Ser
                            325                 330                 335

Phe

<210> SEQ ID NO 7
<211> LENGTH: 1014
<212> TYPE: DNA
<213> ORGANISM: Cucumis sativus

<400> SEQUENCE: 7
atggcttcca agctttgtga ctcgtgtaag tccgcaacag ccactctctt ctgccgtgct      60
gactctgctt tcctttgtct tggctgtgac tccaaagttc acgcagccaa caagcttgcc     120
tctcgccatg ctcgtgtttg ggtttgtgaa gtctgtgagc aagctccggc tcatgtaacc     180
tgtaaggctg acgctgccgc tctctgcctc acttgcgacc acgatattca ctctgctaat     240
ccgctcgcac gtcgtcatga acgtgttcca gttcgccctt ctacgacac atccaactct      300 gacaactcac tccctgttaa acctagcgct gcaatcaact tcctcgacga ccgttacttc     360
tccgatgtcg acgctgatgc cgccgatgtt agtagagaag aagccgaagc tgcttcctgg     420
cttcttccca accctaaccc gaaggcaata gaaagttcag atctgaactc aggcaagttt     480
gagtttccag aaatggatcc ttacctagat ctggattaca gccatgtaga tccgaaatta     540
gaagcgcaag agcagaatag ctccggtgcc gatggagttg ttcctgttca agcaaagga     600 gttcatctct catcagcaaa cgatcgttgc cttggtatag acttcaccgg caccaaatcg     660
ttcccgtacg gtcataaccc tcagtcaatc agtcacagtg tatcatcctc ttcgatcgag     720
gtcggagtgg tgccggacgg gaacgcaatg acagatgtat caaatccgta cacgaaacct     780
tccacagaat cgtctgttca accgctgcaa atctcgccgg cggatcggga agcgagagtg     840
ttaaggtaca gagagaagag gaagaataga aagttcgaga gacgatccg atacgcatct     900 cgtaaagctt acgctgagac gagaccgcga atcaaggac ggttcgccaa acggactgac     960
atcgaacttg atgttgatcg agtgagtgga tacggcgtcg ttcctccgtt ctaa         1014
```

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
ttgaggttgg agttgtgccg                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9
tacctcaaca ctctcgcctc                                              20

<210> SEQ ID NO 10
<211> LENGTH: 22
<212> TYPE: DNA
<213> ORGANISM: Artificial Sequence
<220> FEATURE:
<223> OTHER INFORMATION: Synthetic primer

<400> SEQUENCE: 10
cattctccgt ttggaccttg ct                                           22

<210> SEQ ID NO 11
<211> LENGTH: 26
<212> TYPE: DNA
<213> ORGANISM: Artificial Sequence
<220> FEATURE:
<223> OTHER INFORMATION: Synthetic primer

<400> SEQUENCE: 11
tcgtagtttt ctcaatggag gaactg                                       26

<210> SEQ ID NO 12
<211> LENGTH: 28
<212> TYPE: DNA
<213> ORGANISM: Artificial Sequence
<220> FEATURE:
<223> OTHER INFORMATION: Synthetic primer

<400> SEQUENCE: 12
ccgctcgagg aatggcttcc aagctttg                                     28

<210> SEQ ID NO 13
<211> LENGTH: 29
<212> TYPE: DNA
<213> ORGANISM: Artificial Sequence
<220> FEATURE:
<223> OTHER INFORMATION: Synthetic primer

<400> SEQUENCE: 13
gccgactagt ttagaaggac ggaacgacg                                    29

<210> SEQ ID NO 14
<211> LENGTH: 34
<212> TYPE: DNA
<213> ORGANISM: Artificial Sequence
<220> FEATURE:
<223> OTHER INFORMATION: Synthetic primer

```
<400> SEQUENCE: 14
aaaaagcagg ctccggaatg gcttccaagc tttg                                    34

<210> SEQ ID NO 15
<211> LENGTH: 30
<212> TYPE: DNA
<213> ORGANISM: Artificial Sequence
<220> FEATURE:
<223> OTHER INFORMATION: Synthetic primer

<400> SEQUENCE: 15
agaaagctgg gttagaagga cggaacgacg                                         30

<210> SEQ ID NO 16
<211> LENGTH: 25
<212> TYPE: DNA
<213> ORGANISM: Artificial Sequence
<220> FEATURE:
<223> OTHER INFORMATION: Synthetic primer

<400> SEQUENCE: 16
ttagccctgc cttcatacgc tattt                                              25

<210> SEQ ID NO 17
<211> LENGTH: 25
<212> TYPE: DNA
<213> ORGANISM: Artificial Sequence
<220> FEATURE:
<223> OTHER INFORMATION: Synthetic primer

<400> SEQUENCE: 17
taaataacgt catgcattac atgtt                                              25
```